(12) United States Patent
Karunasiri et al.

(10) Patent No.: US 11,106,230 B2
(45) Date of Patent: Aug. 31, 2021

(54) SYSTEMS AND METHODS FOR AMPLITUDE SHIFT KEYING MODULATION OF A DIGITAL DATA SIGNAL ONTO RADIO FREQUENCY POWER

(71) Applicant: Advanced Bionics AG, Staefa (CH)

(72) Inventors: R. Tissa Karunasiri, Valencia, CA (US); Scott Kenneth Arfin, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 227 days.

(21) Appl. No.: 16/481,829

(22) PCT Filed: Jan. 29, 2018

(86) PCT No.: PCT/US2018/015800
§ 371 (c)(1),
(2) Date: Jul. 29, 2019

(87) PCT Pub. No.: WO2018/140904
PCT Pub. Date: Aug. 2, 2018

(65) Prior Publication Data
US 2020/0057462 A1    Feb. 20, 2020

Related U.S. Application Data

(60) Provisional application No. 62/452,243, filed on Jan. 30, 2017, provisional application No. 62/452,240, filed on Jan. 30, 2017.

(51) Int. Cl.
*H04L 27/04* (2006.01)
*G05F 1/575* (2006.01)
(Continued)

(52) U.S. Cl.
CPC .......... *G05F 1/575* (2013.01); *A61N 1/0541* (2013.01); *A61N 1/36038* (2017.08);
(Continued)

(58) Field of Classification Search
None
See application file for complete search history.

(56) References Cited

U.S. PATENT DOCUMENTS 8,373,386 B2 *  2/2013  Baarman ........... H02J 7/00
                                                320/108
9,444,517 B2 *  9/2016  Teggatz ............ H04L 9/32
                    (Continued)

FOREIGN PATENT DOCUMENTS

CN      104281189       1/2015
CN      104582786       4/2015
EP       1701499        9/2006

OTHER PUBLICATIONS

International Search Report and Written Opinion received in International Application No. PCT/US18/015800, dated Aug. 1, 2018.
(Continued)

*Primary Examiner* — Thomas J. Hiltunen
(74) *Attorney, Agent, or Firm* — ALG Intellectual Property, LLC

(57) ABSTRACT

An amplitude shift keying (ASK) modulation system includes a linear regulator circuit powered by input direct current (DC) power at a first voltage level and that generates regulated DC power at a second voltage level tracking the first voltage level. The system also includes an intermediate DC power switching circuit that receives a digital data signal and selectively couples an intermediate power node with the input DC power at the first voltage level when the digital data signal represents a first binary value, and with the regulated DC power at the second voltage level when the digital data signal represents a second binary value. The ASK modulation system also includes a radio frequency (RF) driver circuit powered by intermediate DC power received at the intermediate power node and that delivers RF
(Continued)

output power representative of the digital data signal to a load at an RF carrier frequency.

20 Claims, 16 Drawing Sheets

(51) Int. Cl.
*A61N 1/36* (2006.01)
*A61N 1/05* (2006.01)
*A61N 1/378* (2006.01)
*G05F 1/59* (2006.01)
*H04L 27/02* (2006.01)
*G05F 1/46* (2006.01)
*H04B 5/00* (2006.01)
*H04R 25/00* (2006.01)
*H03F 3/45* (2006.01)

(52) U.S. Cl.
CPC ......... *A61N 1/36125* (2013.01); *A61N 1/378* (2013.01); *G05F 1/46* (2013.01); *G05F 1/465* (2013.01); *G05F 1/59* (2013.01); *H04B 5/0031* (2013.01); *H04B 5/0037* (2013.01); *H04L 27/02* (2013.01); *H04L 27/04* (2013.01); *H04R 25/55* (2013.01); *H03F 3/45* (2013.01)

(56) References Cited

U.S. PATENT DOCUMENTS

| | | | |
|---|---|---|---|
| 9,570,920 B2* | 2/2017 | Haseno | H02J 50/10 |
| 10,130,812 B2 | 11/2018 | Hartley et al. | |
| 10,199,878 B2* | 2/2019 | Lee | H02J 50/20 |
| 10,886,782 B2* | 1/2021 | Ettes | H02J 50/80 |
| 10,958,106 B2* | 3/2021 | Matsuda | H02J 50/10 |
| 2005/0242794 A1 | 11/2005 | Yen et al. | |
| 2006/0199560 A1 | 9/2006 | Crivelli | |
| 2015/0009240 A1 | 1/2015 | Matsuoka et al. | |
| 2018/0345011 A1* | 12/2018 | Lo | A61N 1/3787 |
| 2021/0111762 A1* | 4/2021 | Lee | H02J 50/12 |

OTHER PUBLICATIONS

First Office Action received in Chinese Patent Application No. 201880009203.3, dated May 27, 2020.

* cited by examiner

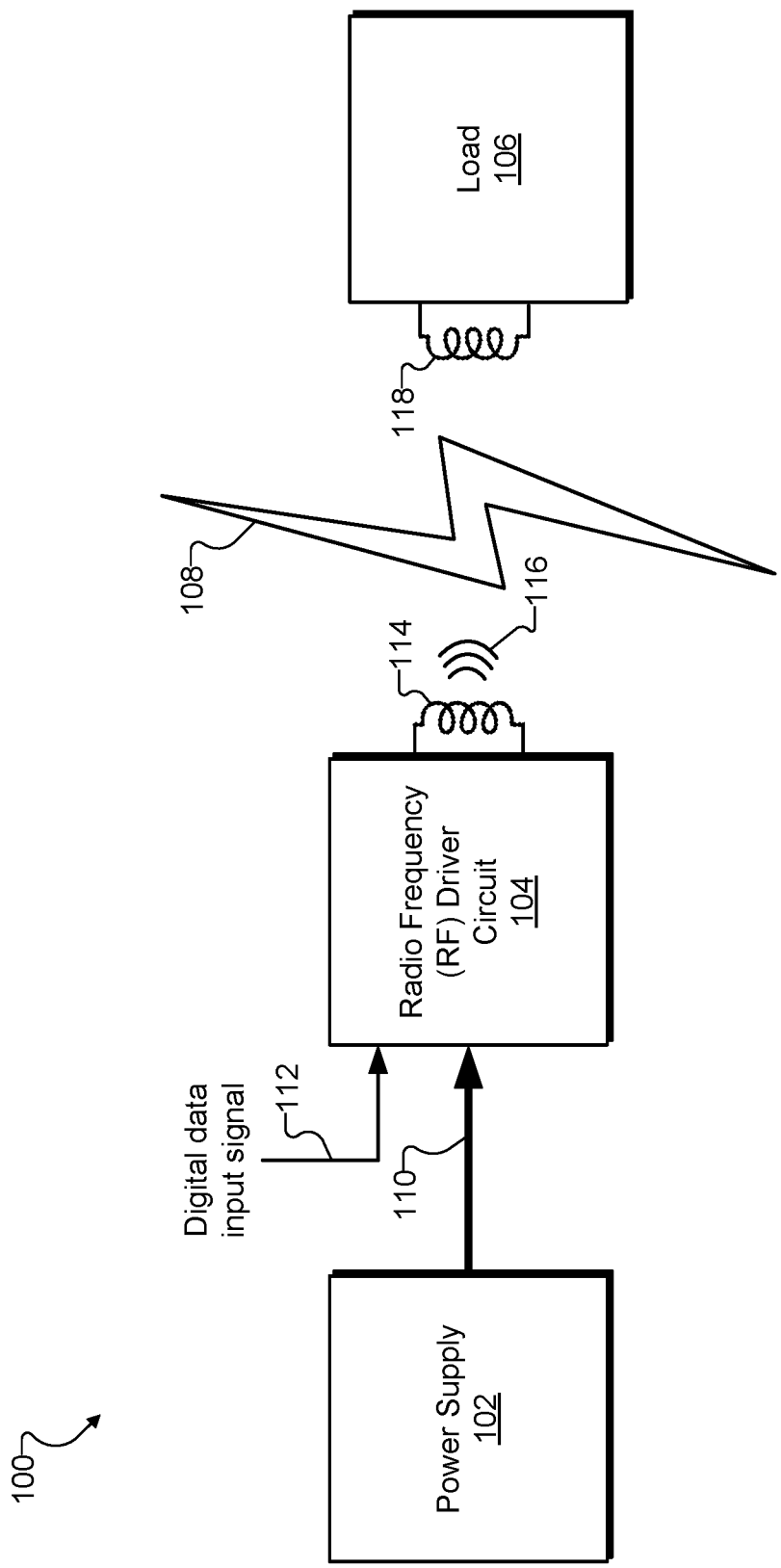

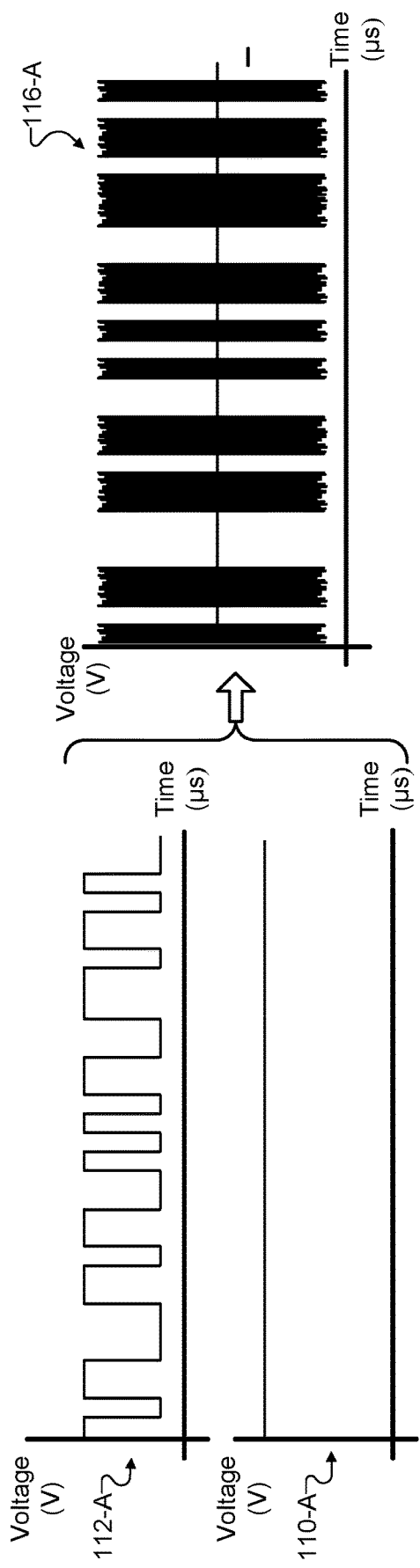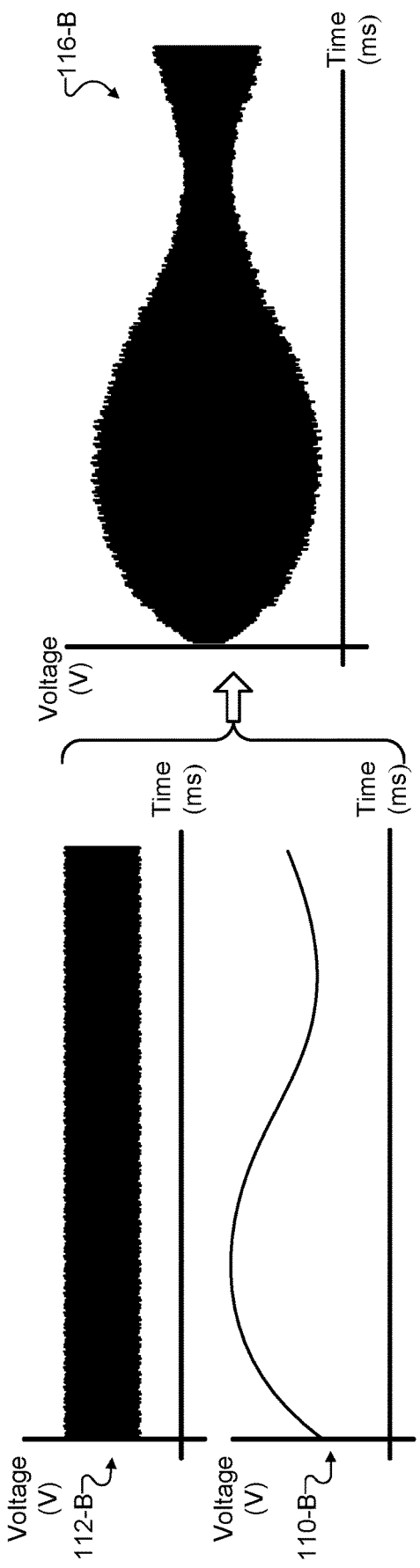
Fig. 3A
Fig. 3B

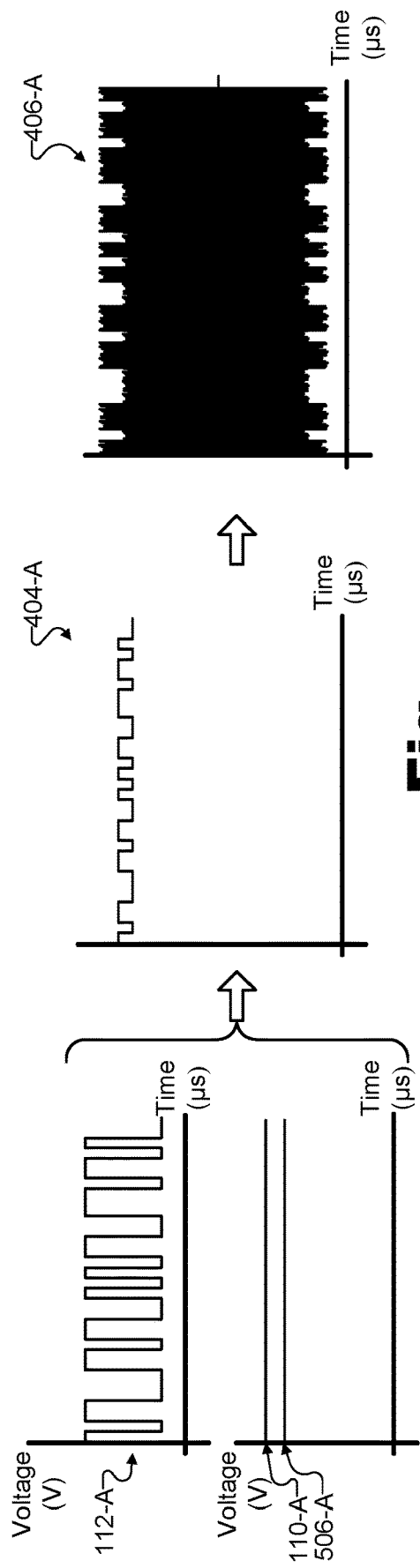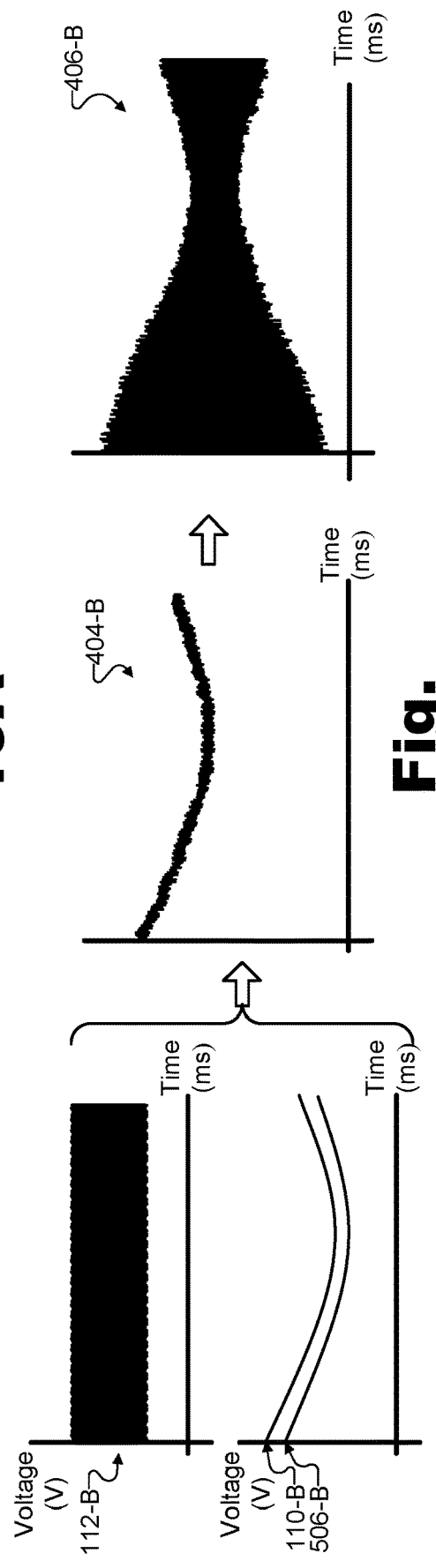

SYSTEMS AND METHODS FOR AMPLITUDE SHIFT KEYING MODULATION OF A DIGITAL DATA SIGNAL ONTO RADIO FREQUENCY POWER

RELATED APPLICATIONS

The present application claims priority to U.S. Provisional Patent Application No. 62/452,243, filed on Jan. 30, 2017 and entitled "Systems and Methods for Amplitude Shift Keying Modulation of a Digital Data Signal onto Radio Frequency Power," and to U.S. Provisional Patent Application No. 62/452,240, filed on Jan. 30, 2017 and entitled "Systems and Methods for Amplitude Shift Keying Modulation of a Digital Data Signal onto Radio Frequency Power." These applications are incorporated herein by reference in their respective entireties.

BACKGROUND INFORMATION

While electrical power is often carried and/or distributed by way of electrical conductors (e.g., wires, etc.), it may be desirable, in certain applications, to deliver electrical power wirelessly. For example, various types of medical devices involve electronic components that are surgically implanted within patients' bodies. Such implants may require electrical power to operate, and yet may lack implanted batteries for generating the electrical power, or may include batteries that periodically require electrical power in order to be recharged. Similarly, it may be convenient or necessary for electronic components in various other applications to be powered wirelessly. To this end, a radio frequency ("RF") driver circuit may generate and deliver electrical power wirelessly over electromagnetic waves in the RF frequency range of the electromagnetic spectrum. Electrical power delivered wirelessly in this way may be referred to as RF power.

In some applications where RF power is distributed from an RF driver circuit to an RF receiver circuit, it may also be desirable for data to be transmitted along with the RF power. For example, a cochlear implant system is one type of medical device system where it is useful to transmit RF power and data together. Specifically, an RF driver circuit within a sound processor of a cochlear implant system that is located external to a patient may transmit RF power and data transcutaneously to a cochlear implant implanted within the patient. The transmitted RF power may be used by the cochlear implant to, for example, stimulate an auditory nerve within the patient according to stimulation parameters represented in the data transmitted along with the RF power.

While RF power and data have been transmitted together in various ways, there remains room for improvement in terms of maximizing the quantity of RF power that may be transmitted with a given amount of data, as well as maximizing the efficiency with which the RF power is transmitted. It would be particularly advantageous to maximize the power transfer quantity and efficiency in applications where the RF driver circuit is powered by a battery (e.g., at a relatively low voltage), and/or where the RF receiver circuit needs a dynamically varying amount of power (e.g., RF power at a dynamically varying voltage level).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 1 illustrates an exemplary implementation of a modulation system that modulates a digital data signal onto radio frequency power that is to be wirelessly delivered to a load according to principles described herein.

FIGS. 3A-3B illustrate exemplary waveforms associated with the modulation of the digital data signal onto the RF power performed by the modulation system of FIG. 1 according to principles described herein.

FIGS. 10A-10B illustrate exemplary waveforms associated with the ASK modulation of the digital data signal onto the RF power performed by the ASK modulation system of FIG. 4 according to principles described herein.

DETAILED DESCRIPTION

Figure 2A:
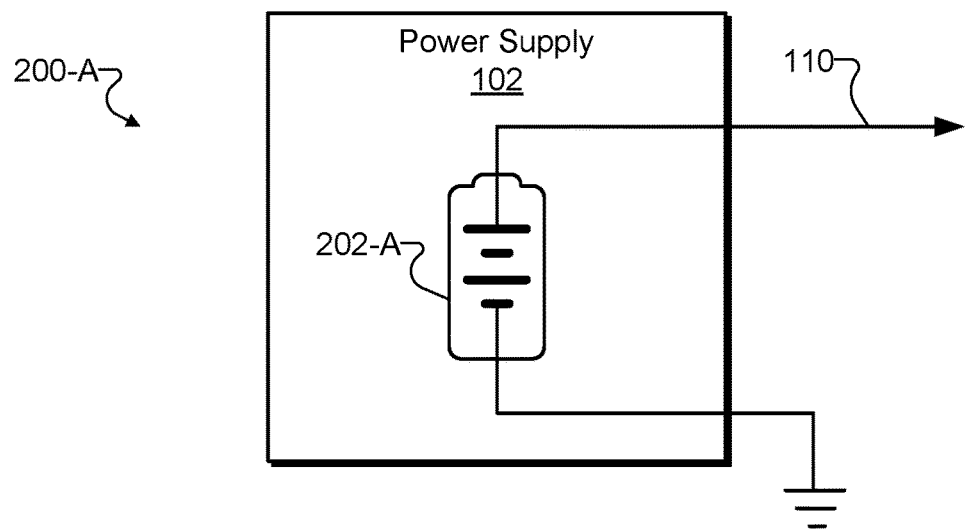
FIGS. 2A-2B illustrate exemplary implementations of power supplies configured to power modulation systems that modulate digital data signals onto RF power that is to be wirelessly delivered to loads according to principles described herein.

Systems and methods for amplitude shift keying ("ASK") modulation of a digital data signal onto radio frequency ("RF") power (e.g., RF power to be wirelessly delivered to a load) are described herein. For example, as will be described and illustrated below, an ASK modulation system may include a linear regulator circuit (e.g., a hybrid linear regulator circuit) powered by input direct current ("DC") power at a first voltage level. The linear regulator circuit may generate regulated DC power at a second voltage level tracking the first voltage level and no greater than the first voltage level. For example, as used herein, the second voltage level may "track" the first voltage level by following the first voltage level ratiometrically (i.e., following at a fixed ratio or percentage from the first voltage level), by following the first voltage level at a fixed voltage offset from the first voltage level, or by following and tracking the first voltage level in other ways that may serve a particular implementation. The ASK modulation system may also include an intermediate DC power switching circuit that receives a digital data signal. When the digital data signal represents a first binary value (e.g., a binary '1' value), the intermediate DC power switching circuit may selectively couple an intermediate power node with the input DC power at the first voltage level based on the digital data signal. Similarly, when the digital data signal represents a second binary value opposite to the first binary value (e.g., a binary '0' value), the intermediate DC power switching circuit may selectively couple the intermediate power node with the regulated DC power at the second voltage level.

The ASK modulation system may further include an RF driver circuit powered by intermediate DC power received by the RF driver circuit at the intermediate power node. For example, depending on whether the digital data signal represents the first or second binary value, the intermediate DC power received by the RF driver circuit may be the input DC power or the regulated DC power that is coupled, by the intermediate DC power switching circuit, onto the intermediate power node. As such, the RF driver circuit may deliver RF output power representative of the digital data signal to a load at an RF carrier frequency.

In the description provided herein, electrical components (e.g., power supplies, driver circuits, loads, etc.) electrical signals (e.g., digital data signals, etc.), circuit nodes (e.g., intermediate power nodes, etc.), electrical power (e.g., input DC power, regulated DC power, etc.), and/or other elements associated with the ASK modulation system and/or circuitry thereof may be said to be "coupled to" or "coupled with" one another. As used herein, a component, a signal, a node, power, and/or another element may be coupled with or coupled to one another by being interconnected in any suitable way (e.g., electrically, wirelessly, communicatively, etc.). For example, a power supply may be said to be coupled with another component by way of a circuit node to which both the power supply and the circuit are coupled. Similarly, as described above, input DC power and regulated DC power may be interchangeably coupled with an intermediate power node based on the toggled switching of the input DC power and the regulated DC power onto the intermediate power node. In other examples, electrical components or devices may be coupled with nodes, power, signals, or other components or devices, electrical signals may be coupled to nodes or to other signals, electrical power may be coupled to nodes or to other electrical power, electrical power and/or signals may be coupled with particular terminals of an electrical component (e.g., a transistor, an amplifier, etc.), and so forth.

Each of the components of the ASK modulation system may be implemented in any manner as may serve a particular implementation. For example, as will be described in more detail below, the linear regulator circuit described above may include a hybrid linear regulator circuit. The hybrid linear regulator circuit may include an input DC power node to which is coupled input DC power at a first variable voltage level (e.g., a voltage level that dynamically varies in time throughout a voltage range defined by a nonzero minimum voltage level and a maximum voltage level at least two times greater than the minimum voltage level), a reference signal node to which is coupled a reference signal at a second variable voltage level (e.g., a voltage level tracking the first variable voltage level and no greater than the first variable voltage level), and an output DC power node by way of which the hybrid linear regulator circuit provides output DC power at the second variable voltage level. For example, this output DC power at this output DC power node of the hybrid linear regulator circuit may be the same as the regulated DC power described above that is alternately coupled (i.e., along with the input DC power) to the intermediate power node by the intermediate DC power switching circuit.

The hybrid linear regulator circuit may further include a high-voltage driver stage coupled to the input DC power node, the reference signal node, and the output DC power node. The high-voltage driver stage may be configured to drive the output DC power at the output DC power node by stepping down the input DC power in accordance with the reference signal and feedback from the output DC power (e.g., a voltage level at which the output DC power is being generated, a current level at which the output DC power is flowing, a power level of the output DC power, or another suitable aspect of the output DC power signal). In particular, the high-voltage driver stage may be configured to drive the output DC power at the output DC power node when the first variable voltage level of the input DC power is greater than a first threshold voltage level (e.g., when the first variable voltage level is relatively high). For example, if the first variable voltage level dynamically varies in time throughout a voltage range from 0.6 V to 3.0 V, the high-voltage driver stage may be configured to drive the output DC power at the output DC power node when the first variable voltage level is greater than approximately 2.0 V.

In parallel with the high-voltage driver stage, the hybrid linear regulator circuit may similarly include a low-voltage driver stage coupled to the input DC power node, the reference signal node, and the output DC power node. The low-voltage driver stage may similarly be configured to drive the output DC power at the output DC power node by stepping down the input DC power in accordance with the reference signal and the feedback from the output DC power. However, the low-voltage driver stage may be configured to drive the output DC power at the output DC power node when the first variable voltage level of the input DC power is less than a second threshold voltage level (e.g., when the first variable voltage level is relatively low). For example, if the first variable voltage level dynamically varies in time throughout a voltage range from 0.6 V to 3.0 V, the high-voltage driver stage may be configured to drive the output DC power at the output DC power node when the first variable voltage level is less than approximately 1.6 V.

Similarly, if the first variable voltage level is between the first and second thresholds (e.g., between 1.6 V and 2.0 V in the example above), both the high-voltage driver stage and the low-voltage driver stage may mutually (e.g., cooperatively, jointly, in parallel, etc.) drive the output DC power at the output DC power node.

It will be understood that the voltage ranges and voltage level thresholds given in this example are exemplary only and that the voltage ranges and thresholds that may apply with respect to a particular implementation may be different from the examples given. Additionally, the voltage thresholds may be loosely defined such that there is a smooth transition from the low-voltage driver stage unilaterally driving the output DC power when the first variable voltage level is at a lower limit (e.g., 0.6 V), to the low-voltage driver stage and the high-voltage driver stage mutually driving the output DC power when the first variable voltage level is at a mid-range level, to the high-voltage driver stage unilaterally driving the output DC power when the first voltage level is at an upper limit (e.g., 3.0 V). Examples of hybrid linear regulator circuits will be described in more detail below.

The systems and methods described herein for ASK modulation of a digital data signal onto RF power that is to be wirelessly delivered to a load may provide various benefits. For example, by delivering power wirelessly, an RF driver circuit may provide RF power to places where it may be difficult or impossible to deliver power over electrical conductors such as wires (e.g., to devices implanted within patients or disposed in other difficult to access places). Moreover, by modulating a digital data signal onto the RF power transmitted to the difficult-to-reach places, instructions and/or other data may be provided as part of the power delivery such that additional data signals may not be needed. For instance, in the case of a cochlear implant system in which an external sound processor transmits RF power to an internally implanted cochlear implant, the RF power may be modulated with digital data representative of stimulation parameters directing the cochlear implant to apply stimulation to the patient. No standalone data signal may need to be transmitted to the cochlear implant because the data may all be ASK modulated onto the RF power being transmitted.

Additionally, the systems and methods for ASK modulation of a digital data signal onto RF power described herein may provide significant benefits and advantages compared to other systems and methods for ASK modulation. For instance, by modulating the digital data onto the RF output power using a relatively low modulation depth as described herein, the systems and methods may conveniently provide a larger amount of power for a given first voltage level, increasing the overall efficiency and capability of the systems. This may be particularly beneficial with new generations of technology where lower power and/or larger amounts of data are demanded. For example, certain cochlear implant systems may include sound processors that are designed to consume very little power (e.g., so as to decrease the size of the sound processor by decreasing the battery size). However, such sound processors may still be responsible for providing a certain amount of power to cochlear implants in order for the cochlear implants to provide proper stimulation to patients in various situations (e.g., even when loud sounds requiring relatively large amounts of stimulation energy are represented). Due to the increased power output and efficiency provided by the present systems and methods, such cochlear implant systems may be able to provide desirable amounts of power and data to the cochlear implants even when relatively small batteries with relatively low voltages, less capacity, etc., are being used. The increased efficiency may also provide similar benefits in other types of applications besides cochlear implant systems.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary implementation of a modulation system 100 that modulates a digital data signal onto RF power that is to be wirelessly delivered to a load. As shown, modulation system 100 includes a power supply 102 coupled with an RF driver circuit 104 that is wirelessly and communicatively coupled with a load 106. As will be described, power supply 102 and RF driver circuit 104 may provide RF power modulated with digital data to load 106 through a barrier 108 that is disposed between RF driver circuit 104 and load 106. As such, load 106 may receive the RF power and the digital data and use the RF power and digital data to perform any operations as may serve a particular implementation. Each of the elements of modulation system 100 and the communications therebetween will now be described in more detail.

Power supply 102 may generate, prepare, and supply electrical power for use by modulation system 100, and may be implemented by any power supply as may serve a particular implementation. To illustrate, FIGS. 2A-2B illustrate exemplary implementations 200 (i.e., implementation 200-A in FIG. 2A and implementation 200-B in FIG. 2B) of power supply 102 that may be configured to power modulation system 100.

Figure 2B:
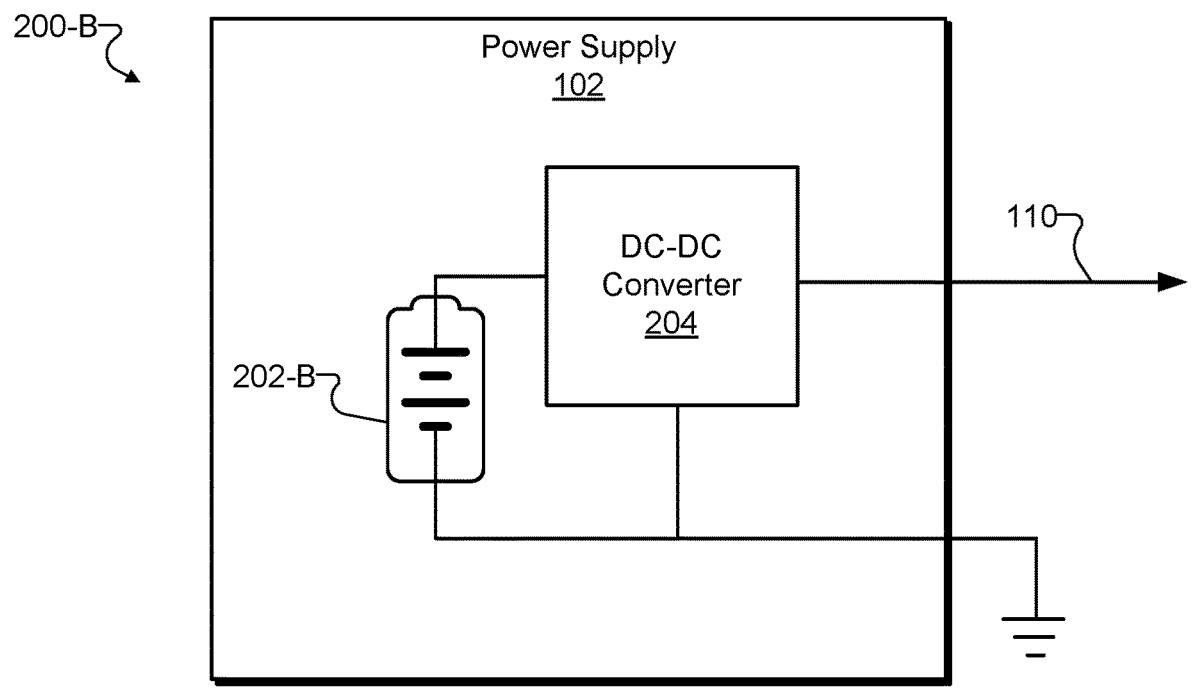

Implementation 200-A of FIG. 2A, for example, illustrates an implementation of power supply 102 that includes merely a battery 202-A. Battery 202-A may include at least one electric battery generating battery power at a battery voltage level. In other examples, it will be understood that battery 202-A and/or other batteries described herein may additionally or alternatively include and/or be implemented by other types of electric power cells other than batteries. For example, in certain implementations, battery 202-A may be implemented by an electric solar cell that generates electric power at an electric power cell voltage level based on energy received from ambient light or other such sources. As such, the electric power generated by any type of electric power cell may be analogous to battery power generated by the batteries described herein. Similarly, the electric power cell voltage level may be analogous to battery voltage levels described herein.

Battery 202-A may be implemented by any suitable number of primary (i.e., non-rechargeable) or secondary (i.e., rechargeable) batteries as may serve a particular implementation. For example, battery 202-A may be implemented by one or more alkaline batteries, one or more lithium-ion batteries, one or more zinc-air batteries, or the like.

In some examples, the type of battery may be selected for and/or designed into a circuit based on particular characteristics of the battery such as a size and/or weight of the battery, an energy density of the battery, an output voltage of the battery, an instantaneous current or power that may be sourced by the battery, or any other characteristic as may serve a particular implementation. For example, in certain cochlear implant system implementations, one or more zinc-air batteries may be selected for use due to their relatively high energy density and relatively small size. Because these batteries happen to also be characterized by a relatively low output voltage and low instantaneous power sourcing capabilities, cochlear implant systems employing zinc-air batteries may require or benefit from the increased efficiency provided by the systems and methods described herein.

Regardless of the chemistry, type, or number of batteries used to implement battery 202-A, battery 202-A may provide DC power at a voltage level that is greater than a voltage level of ground (e.g., greater than 0 V). Thus, as shown, battery 202-A may be connected to ground and to a DC power terminal to which input DC power 110 is coupled. As will be described in more detail below, input DC power 110 may be used to power various other circuits and system components of modulation system 100. For example, as illustrated by FIGS. 1 and 2A, battery 202-A may be coupled to RF driver circuit 104 and input DC power 110 may be the battery power. As such, the voltage level of input DC power 110 (e.g., commonly referred to herein at the first voltage level), may be the battery voltage level.

In implementations where a single battery is used to implement battery 202-A, input DC power 110 may be driven at a voltage level equal to the output voltage of the battery implementing battery 202-A. For instance, a single zinc-air battery may provide voltage at 1.2 V when the battery is fresh (i.e., fully charged) and may gradually decrease in output voltage as the battery is consumed. Accordingly, input DC power 110 may be driven at 1.2 V for a time and then may gradually decrease to, for example, 0.6 V before being replaced or recharged.

In implementations where a plurality of batteries is used to implement battery 202-A, on the other hand, input DC power 110 may be driven at a voltage level equal to the sum of the output voltage of all the batteries implementing battery 202-A (e.g., if the batteries are connected in series). For instance, two zinc-air batteries may provide voltage at 1.2 V each when they are fresh and then gradually decrease in output voltage as the batteries are consumed. Thus, input DC power 110 may be driven at 2.4 V when the batteries are fresh and then gradually decrease until being replaced. If circuitry relying on input DC power 110 is configured to operate on a relatively low voltage (e.g., such as 0.6 V), the batteries implementing battery 202-A may decrease significantly before modulation system 100 will cease to operate properly.

Implementation 200-B of FIG. 2B illustrates a different implementation of power supply 102 that includes, along with a battery 202-B, a DC-DC converter 204. Battery 202-B may include at least one electric battery generating battery power at a battery voltage level. For example, battery 202-B may include one or more of any of the same types of batteries described above in relation to battery 202-A.

DC-DC converter 204 may be disposed in the circuitry of power supply 102 and may represent any converter that alters (e.g., steps up, steps down, etc.) the voltage level provided by battery 202-B in order to provide input DC power 110 at a first voltage level that is different from the output voltage of battery 202-B.

For example, DC-DC converter 204 may include or be implemented by a charge pump circuit that steps up the battery voltage level (i.e., the output voltage level of battery 202-B) to, for instance, generate input DC power 110 at the first voltage level. In other instances, the charge pump circuit may step up the battery voltage level to generate stepped-up battery power at a stepped-up battery voltage level (e.g., a voltage level different from the first voltage level). Such stepped-up battery power may be used for powering a switching regulator circuit (e.g., that is also included as part of DC-DC converter 204) that regulates the stepped-up battery power at the stepped-up battery voltage level to generate input DC power 110 at the first voltage level.

In the same or other examples, DC-DC converter 204 may include or be implemented by a switching regulator circuit powered by the battery power at the battery voltage level. The switching regulator circuit may regulate the battery power at the battery voltage level to generate input DC power 110 at the first voltage level. In certain implementations, the first voltage level of input DC power 110 generated by the switching regulator circuit within DC-DC converter 204 may be a variable voltage level dynamically varying in time within a static voltage range defined by a nonzero minimum voltage level (e.g., 0.6 V) and a maximum voltage level at least two, three, four, or even more times greater than the minimum voltage level (e.g., 3.0 V). For example, the switching regulator circuit included within DC-DC converter 204 may receive a power delivery signal representative of a power delivery parameter, and may generate the input DC power in accordance with the power delivery parameter by causing the variable voltage level of input DC power 110 to dynamically vary based on the power delivery parameter. Examples of power delivery parameters and variable voltage levels of input DC power 110 will be described in more detail below.

Returning to FIG. 1, input DC power 110 is supplied by power supply 102 to RF driver circuit 104 along with a digital data input signal 112 ("digital data signal 112"), which may be generated elsewhere within a system that includes modulation system 100. For example, if modulation system 100 is included within a sound processor of a cochlear implant system, digital data signal 112 may be a digital data signal representative of commands to be performed by a cochlear implant implanted within a patient, and may be generated by a processor included elsewhere within the sound processor of the cochlear implant system. Whatever the application, digital data signal 112 may be generated for the purpose of being transmitted along with RF power being wirelessly delivered to load 106.

RF driver circuit 104 may modulate digital data signal 112 onto input DC power 110 to wirelessly deliver (i.e., transmit) RF power that derives from input DC power 110 and is representative of digital data signal 112 to load 106. RF driver circuit 104 may be implemented in any way as may serve a particular implementation. For example, RF driver circuit 104 may include a Class D amplifier that receives a signal representative of an RF carrier frequency (e.g., a 49 MHz sine wave generated by a crystal oscillator circuit or the like) as an input. Powered by input DC power 110 and using an antenna 114, the Class D amplifier may generate and transmit RF output power 116 to be wirelessly delivered through barrier 108 and to be received by load 106 using an antenna 118. As shown, RF output power 116 is delivered wirelessly (i.e., across barrier 108) from RF driver circuit 104 to load 106. As will be described and illustrated in more detail below, RF output power 116 may not only include RF power that is delivered to load 106 but may also include a wireless data signal modulated onto the RF power. Thus, by way of RF output power 116, digital data (e.g., digital data represented in digital data signal 112) may be transmitted to load 106. In some examples, load 106 may also use the power included in RF output power 116 to communicate a digital data signal back to a receiver on the side of barrier 108 opposite load 106.

Load 106 may be any suitable device, sensor, or other component that may be configured to receive and demodulate RF output power 116 to thereby to receive and use the wireless power and wireless data signal that are included within RF output power 116. For example, load 106 may be implemented by a medical device implanted within a patient (e.g., a cochlear implant or the like), a sensor operating in a difficult-to-access location (e.g., within a motor block or the like), and/or any other load as may serve a particular implementation. In certain implementations, load 106 may be powered directly by the wireless power included in RF output power 116, while in other implementations load 106 may be powered or partially powered by a battery which may be recharged by the wireless power. Examples of loads that may implement load 106 will be described below.

Barrier 108 may be any barrier, medium, or the like that stands between RF driver circuit 104 and load 106. For example, if load 106 is a medical device such as a cochlear implant, barrier 108 may include skin of the patient through which RF output power 116 may be transmitted. In other examples, barrier 108 may include another solid barrier or may simply include air, a vacuum, or the like.

To illustrate modulation system 100 in operation, FIGS. 3A-3B show exemplary waveforms associated with the modulation of digital data signal 112 onto RF power 116. More specifically, FIG. 3A illustrates the modulation on a relatively short timescale (e.g., in microseconds), while FIG. 3B illustrates the modulation on a relatively long timescale (e.g., in milliseconds). Thus, in some examples, certain features illustrated in FIG. 3B may take place over a timescale several (e.g., three or more) orders of magnitude greater than a timescale over which certain features illustrated in FIG. 3A may take place.

FIG. 3A shows a relatively short segment 112-A of digital data signal 112 and a relatively short segment 110-A of input DC power 110, described above in relation to FIG. 1. For example, segment 112-A of digital data signal 112 may be toggling between binary values (i.e., '1' and '0', "HIGH" and "LOW", etc.) with edges that occur in nanoseconds (i.e., less than a microsecond). Each bit represented within segment 112-A may be represented for a relatively short period of time (e.g., one or two microseconds), such that the entirety of segment 112-A illustrated in FIG. 3A may take place over approximately thirty to sixty microseconds or so. Segment 110-A may take place over the same amount of time and, as such, may look to be relatively stable at an unchanging voltage level.

Powered by input DC power 110, RF driver circuit 104 may generate and transmit RF output power 116, a segment 116-A of which is illustrated in FIG. 3A. The length (in terms of time) of segment 116-A of RF output power 116 may be the same as the lengths of segments 112-A and 110-A. Accordingly, as shown, segment 116-A may include periods of approximately one to two microseconds each where RF output power is being transmitted at an RF carrier frequency (e.g., 49 MHz or another frequency corresponding to a period significantly shorter than the one or two microsecond period of the digital data signal) to represent, for example, a binary '1', and similar periods where no RF output power is being transmitted to represent, for example, a binary '0'. As such, segment 116-A shows how RF output power 116 may deliver wireless power to the load that is representative of digital data signal 112. However, segment 116-A also illustrates that RF output power 116 only provides wireless power about half the time because no wireless power is transmitted to represent a binary '0'.

FIG. 3B shows a relatively long segment 112-B of digital data signal 112 and a relatively long segment 110-B of input DC power 110. Digital data signal 112 and input DC power 110 may be changing at the same rates as described with respect to FIG. 3A, but, because of the relatively long timescale, may be much more compressed as compared to the waveforms of FIG. 3A. For example, each bit represented within segment 112-A may be represented for one or two microseconds. However, segment 112-B may take place over several tens of milliseconds (e.g., 50 milliseconds), making the time represented by segment 112-B approximately three orders of magnitude larger than the time represented by segment 112-A. As such, thousands of toggles between the binary '1' and the binary '0' of digital data signal 112 may be represented by segment 112-B. Segment 110-B may take place over the same amount of time as segment 110-A and, on the longer timescale, is shown to vary in time. For example, as described above, input DC power 110 may vary in time over a relatively wide voltage range (e.g., a voltage range defined by a nonzero minimum voltage level and a maximum voltage level at least two times greater than the minimum voltage level, such as from 0.6 V to 3.0 V). Thus, as shown, segment 110-B of input DC power 110 may vary in time, but may change much more gradually than does digital data signal 112.

As described above, input DC power 110 may vary based on input from a power delivery parameter which may represent, for example, a loudness of a sound that is to be represented to a patient by a cochlear implant generating electrical stimulation. Because the loudness of sounds detected by a cochlear implant system may change on a millisecond timescale, rather than a microsecond timescale, the power delivery parameter (and input DC power 110 following the power delivery parameter) may change much more slowly than digital data signal 112.

Segment 116-B shows a segment of RF output power 116 with the same length (in terms of time) as the lengths of segments 112-B and 110-B. Segment 116-B may include periods of approximately one to two microseconds each where RF output power is being transmitted at the RF carrier frequency (e.g., 49 MHz or another frequency corresponding to a period significantly shorter than the one to two microsecond period of digital data signal 112) to represent, for example, a binary '1', and similar periods where no RF output power is being transmitted to represent, for example, a binary '0'. However, because of the relatively long timescale, such toggling cannot be seen in segment 116-B. However, segment 116-B does illustrate that RF output power 116 may increase (i.e., provide power at larger and larger voltage levels) and diminish (i.e., provide power at smaller and smaller voltage levels) in accordance with the changing of input DC power 110 illustrated by segment 110-B. As such, segment 116-B shows how RF output power 116 may deliver differing amounts of wireless power to the load based on what the load may require (i.e., based on the power delivery parameter).

As mentioned above, and as is most readily apparent from FIG. 3A, modulation system 400 may modulate digital data signal 112 onto RF output power 116, but may only deliver power approximately half the time (e.g., when the digital data being represented on digital data signal 112 is a binary '1'). Sufficient RF power may be provided for certain loads in this way, depending on various factors such as the voltage level of input DC power 110, the power requirements of the load, and so forth. For other loads, however, it may be desirable or necessary to transmit more RF power than may be transmitted by modulation system 100. Specifically, modulation system 100 may be considered to be implementing on-off keying modulation or ASK modulation at a modulation depth of 100% (i.e., toggling between 100% RF power and 0% RF power). However, it may be preferable to ASK modulate digital data signal 112 onto RF output power 116 at a lower modulation depth such as, for example, 10% (i.e., to toggle between 100% RF power and 90% RF power) to that more power may be efficiently delivered to the load in accordance with what the load needs to operate properly.

Figure 4:
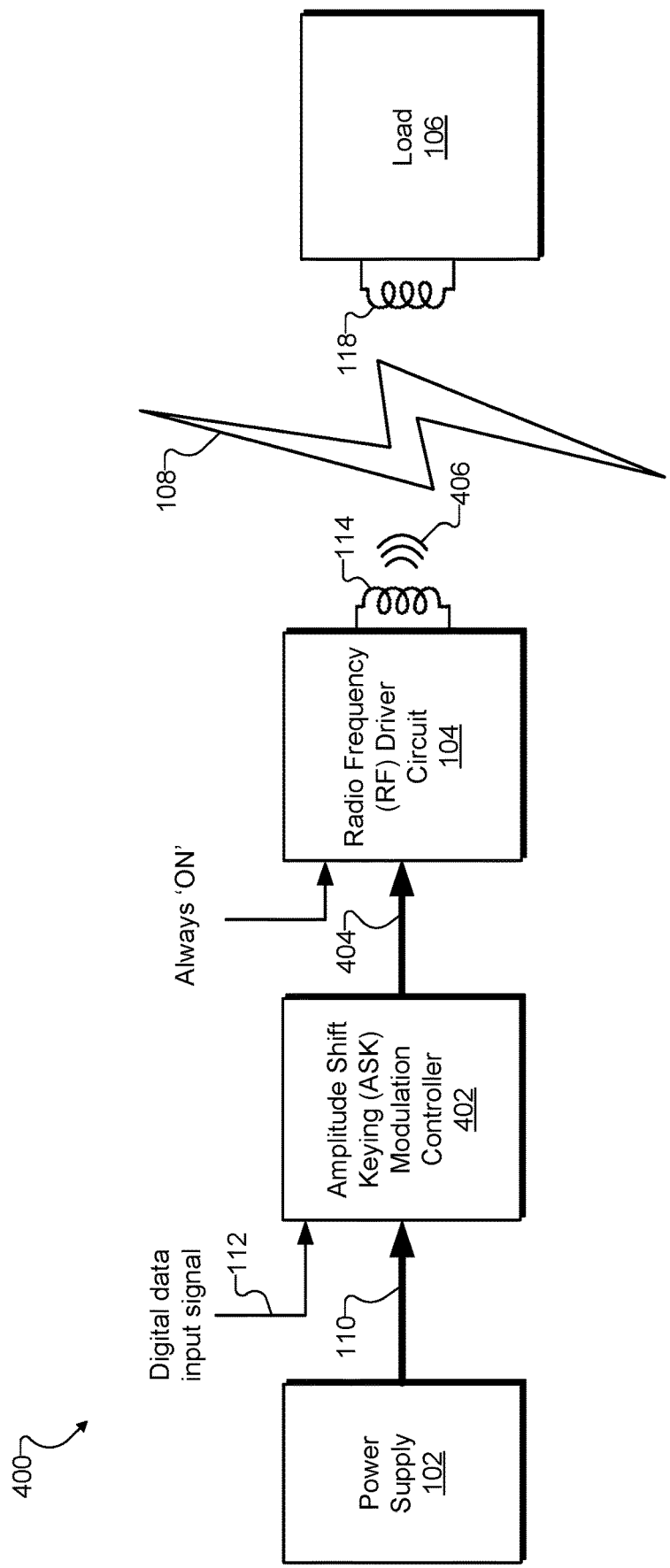
FIG. 4 illustrates an exemplary implementation of an amplitude shift keying ("ASK") modulation system for ASK modulation of a digital data signal onto RF power that is to be wirelessly delivered to a load according to principles described herein.

To this end, FIG. 4 illustrates an exemplary implementation of an ASK modulation system 400 for ASK modulation of digital data signal 112 onto RF power that is to be wirelessly delivered to a load. In contrast with modulation system 100, ASK modulation system 400 may be configured to ASK modulate digital data signal 112 onto RF power with a modulation depth other than a modulation depth of 100%. For example, as will be described below, ASK modulation system 400 may ASK modulate digital data signal 112 onto RF power with any of a plurality of modulation depths that may be selectable and reconfigurable to serve a particular implementation.

As shown in FIG. 4, ASK modulation system 400 may include several of the same components described above in relation to modulation system 100, including a power supply 102 that supplies input DC power 110, a digital data input signal 112, and an RF driver 104 (including an antenna 114) separated, by a barrier 108, from a load 106 (including an antenna 118). These components may perform similar or identical functions in similar ways as described above in relation to modulation system 100.

However, as further shown in FIG. 4, ASK modulation system 400 may also include various elements that are not included in modulation system 100. For example, in ASK modulation system 400, an ASK modulation controller 402 is inserted after power supply 102 to generate an intermediate DC power 404 to power RF driver 104. As will be described and illustrated below, ASK modulation controller 402 may generate intermediate DC power 404 to toggle, in accordance with digital data signal 112, between input DC power 110 at a first voltage level (e.g., a first variable voltage level that dynamically varies within a static voltage range such as from 0.6 V to 3.3 V) and a regulated DC power at a second voltage level tracking the first voltage level and no greater than the first voltage level (e.g., a second variable voltage level that dynamically varies to constantly follow the first variable voltage level ratiometrically, at a fixed offset below the first variable voltage level, or in a similar way).

In ASK modulation system 400, RF driver 104 is thus not toggled to generate power and stop generating power as was described in relation to modulation system 100 and as shown, for example, in FIG. 3A. Rather, in ASK modulation system 400, RF driver 104 is set to be "Always 'ON'" (i.e., so that RF output power is always being transmitted), but is powered by an input DC power that is toggling between the first and second voltage levels. Accordingly, the modulation depth of ASK modulation system 400 may be configured simply by changing the second voltage level with respect to the first voltage level (i.e., the two voltage levels between which intermediate DC power 404 is being toggled). Ultimately, as with modulation system 100, RF output power representative of digital data signal 112 may be generated and delivered to load 106 at an RF carrier frequency. Specifically, an RF output power 406 may be delivered that includes not only RF power but also includes a digital data signal (e.g., data representative of digital data signal 112) modulated onto the RF power. It will be noted, however, that RF output power 406 delivered by ASK modulation system 400 may include a significantly larger amount of wireless power for a given first variable voltage level than may be included within RF output power 116 delivered by modulation system 100.

Figure 5:
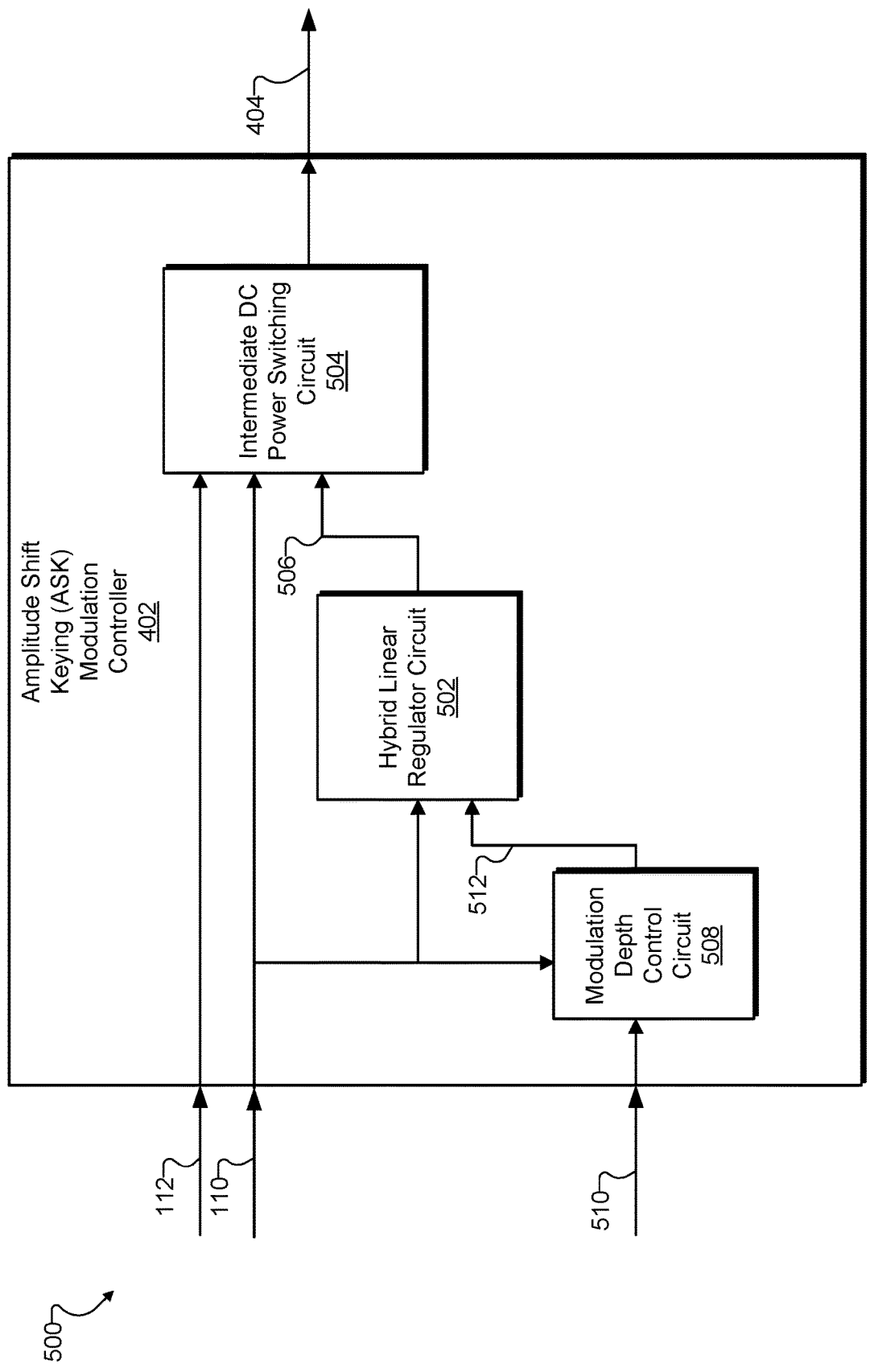
FIG. 5 illustrates an exemplary implementation of an ASK modulation controller included within the ASK modulation system of FIG. 4 according to principles described herein.

FIG. 5 illustrates an exemplary implementation 500 of ASK modulation controller 402 included within ASK modulation system 400. As shown, ASK modulation controller 402 includes a hybrid linear regulator circuit 502 and an intermediate DC power switching circuit 504 that receives a regulated DC power 506 (e.g., a regulated DC power at the second voltage level tracking the first voltage level) generated by hybrid linear regulator circuit 502. ASK modulation controller 402 further includes a modulation depth control circuit 508 that receives a modulation depth select signal 510 representative of a particular ASK modulation depth in a plurality of ASK modulation depths supported by modulation depth control circuit 508. Based on the modulation depth select signal 510 and the first voltage level of input DC power 110, modulation depth control circuit 508 generates a reference signal 512 at the second voltage level. Hybrid linear regulator circuit 502 may use reference signal 512 to generate regulated DC power 506 at the second voltage level.

Each of the circuits shown in implementation 500 of ASK modulation controller 402 will now be described in more details.

Hybrid linear regulator circuit 502 may generate regulated DC power 506 based on power received from input DC power 110 and based on reference signal 512. In particular, hybrid linear regulator circuit 502 may be specially configured to generate regulated DC power 506 even when respective voltage levels of input DC power 110 and reference signal 512 dynamically vary in time throughout a relatively wide voltage range.

For example, input DC power 110 may be at a first variable voltage level that dynamically varies within a voltage range defined by a nonzero minimum voltage level and a maximum voltage level at least two times greater (e.g., two times greater, three times greater, four times greater or more), than the minimum voltage level. Additionally or alternatively, the minimum voltage level may be less than 1.0 V and the maximum voltage level may be at least 2.0 V greater than the minimum voltage level. For instance, in one example, the minimum voltage level may be approximately 0.6 V and the maximum voltage level may be approximately 3.0 V (i.e., five times greater and 2.4 V greater than 0.6 V). Similarly, reference signal 512 may dynamically vary in time throughout a relatively wide voltage range in order to stay at a second variable voltage level that tracks (e.g., is ratiometric with, follows at a fixed offset from, etc.) the first voltage level (e.g., 90% of the first voltage level, 0.5 V below the first voltage level, etc.). Thus, for example, reference signal may be at 2.7 V when input DC power 110 is at 3.0 V, 1.8 V when input DC power 110 is at 2.0 V, 0.9 V when input DC power 110 is at 1.0 V, and so on.

Traditional linear regulator circuits may be configured to regulate power when voltage levels of the input and output power are both relatively high (e.g., around 1.5-3.0 V) or are both relatively low (e.g., around 0.6-1.5 V). However, traditional linear regulator circuits are not typically configured to regulate power when the voltage levels of both the input and output power are dynamically varying, and particularly when the voltage levels dynamically vary throughout a voltage range that includes both relatively high and relatively low voltage levels. Hybrid linear regulator circuit 502 may be configured to regulate power even when both input DC power 110 and regulated DC power 506 are dynamically varying throughout such a wide voltage range by applying a two-stage approach.

Figure 6:
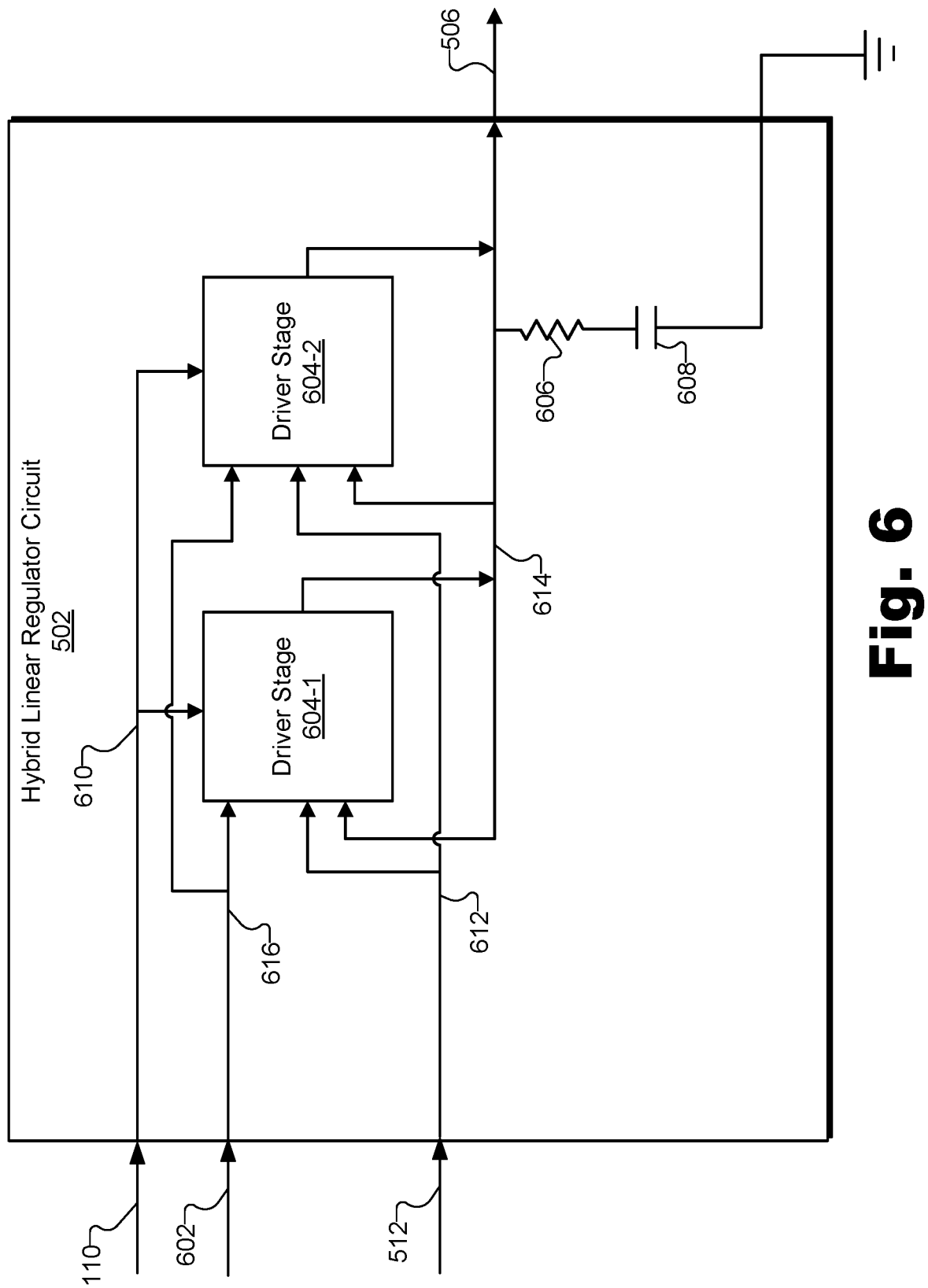
FIGS. 6-7 illustrate exemplary implementations of the hybrid linear regulator circuit of the ASK modulation controller of FIG. 5 according to principles described herein.
Figure 7:
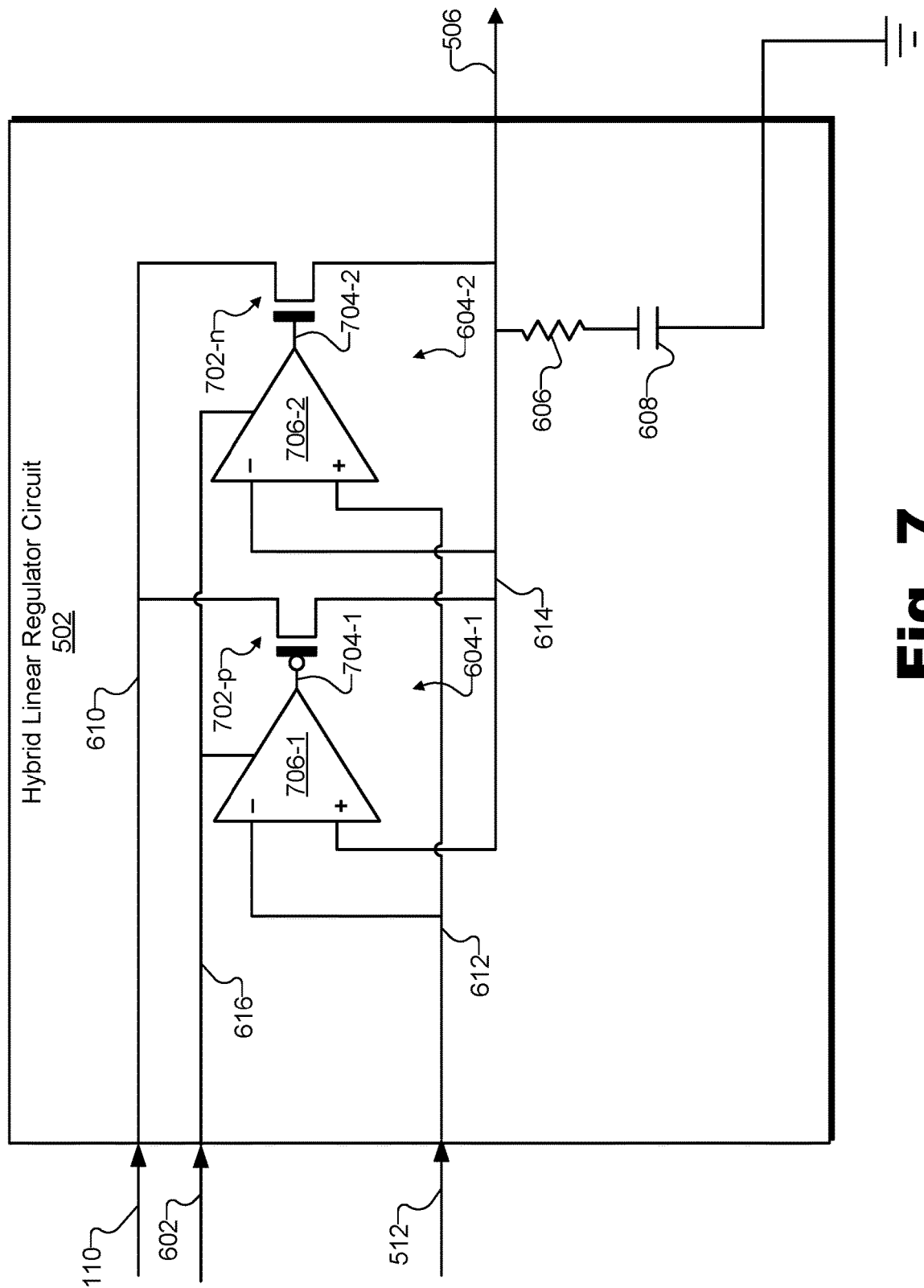

To illustrate, FIGS. 6 and 7 show exemplary implementations of hybrid linear regulator circuit 502. More particularly, FIG. 6 shows that hybrid linear regulator circuit 502 receives input DC power 110, reference signal 512, and an auxiliary DC power 602 as inputs. These inputs, along with feedback from regulated DC power 506 each go into parallel driver stages 604 (i.e., high-voltage driver stage 604-1 and low-voltage driver stage 604-2). Either or both of driver stages 604 generate regulated DC power 506 in conjunction with an RC circuit having a resistor 606 and a capacitor 608 that filters and otherwise prepares regulated DC power 506 for use by other components within ASK modulation system 400.

More specifically, FIG. 6 illustrates that hybrid linear regulator circuit 502 includes an input DC power node 610 to which input DC power 110 (e.g., at the first variable voltage level) is coupled, a reference signal node 612 to which reference signal 512 (e.g., at the second variable voltage level) is coupled, and an output DC power node 614 by way of which the system provides output DC power (i.e., regulated DC power 506) at the second variable voltage level. Hybrid linear regulator circuit 502 further includes high-voltage driver stage 604-1 coupled to input DC power node 610, reference signal node 612, and output DC power node 614. High-voltage driver stage 604-1 may be configured to drive regulated DC power 506 at output DC power node 614 when the first variable voltage level of input DC power 110 is greater than a first threshold voltage level by stepping down input DC power 110 in accordance with reference signal 512 and feedback from regulated DC power 506. For example, the first threshold voltage level may be at a mid-point of the voltage range throughout which the first variable voltage level dynamically varies, a predetermined voltage associated with performance specifications of components included within high-voltage driver stage 604-1, or any other suitable threshold as may serve a particular implementation. As a concrete example for purposes of explanation, for instance, the first threshold voltage level may be 2.3 V. Thus, in this example, when the first variable voltage level is greater than 2.3 V, high-voltage driver stage 604-1 may drive regulated DC power 506 (e.g., alone or mutually with low-voltage driver stage 604-2).

As shown, hybrid linear regulator circuit 502 also includes low-voltage driver stage 604-2 coupled (in parallel with high-voltage driver stage 604-1) to input DC power node 610, reference signal node 612, and output DC power node 614. Low-voltage driver stage 604-2 may be configured to drive regulated DC power 506 at output DC power node 614 when the first variable voltage level of input DC power 110 is less than a second threshold voltage level by stepping down input DC power 110 in accordance with reference signal 512 and the feedback from regulated DC power 506. For example, the second threshold voltage level may be at a mid-point of the voltage range throughout which the first variable voltage level dynamically varies, a predetermined voltage associated with performance specifications of components included within low-voltage driver stage 604-2, or any other suitable threshold as may serve a particular implementation. In some examples, the second threshold voltage level may be less than the first threshold voltage level, while, in other examples, the second threshold voltage level may be equal to or greater than the first threshold voltage level. As a concrete example for purposes of explanation, for instance, the second threshold voltage level may be 1.3 V. Thus, in this example, when the first variable voltage level is less than 1.3 V, low-voltage driver stage 604-2 may drive regulated DC power 506 (e.g., alone or mutually with high-voltage driver stage 604-1).

As shown in FIG. 6, along with input DC power node 610, reference signal node 612, and output DC power node 614, hybrid linear regulator circuit 502 may further include an auxiliary power node 616 to which auxiliary DC power 602 may be coupled. Auxiliary DC power 602 may be driven at a static voltage level no smaller than the maximum voltage level defining the voltage range throughout which the first variable voltage level dynamically varies. For example, if the first variable voltage level of input DC power 110 varies throughout the voltage range from 0.6 V to 3.0 V, auxiliary DC power 602 may be driven at a static voltage such as 3.0 V or another level greater than 3.0 V. Auxiliary DC power 602 may be generated by power supply 102 or by any other suitable component within ASK modulation system 400. In some examples, auxiliary DC power 602 may be derived from input DC power 110, but, in contrast with regulated DC power 506, may not track the voltage level of input DC power 110 (i.e., the first variable voltage level) but rather may be driven at the static voltage level. As will be described in more detail below, auxiliary DC power 602 may power certain components of driver stages 604 to facilitate driver stages 604 in performing the operations described herein.

Resistor 606 may operate as part of an RC circuit with capacitor 608 to properly filter and otherwise prepare regulated DC power 506 for use by other components within ASK modulation system 400. For example, resistor 606 and capacitor 608 may be selected with values configured to allow regulated DC power 506 to be relatively stable and smooth in spite of switching performed by intermediate DC power switching circuit 504 while simultaneously allowing regulated DC power 506 to be responsive to changes in the first voltage level of input DC power 110 so that regulated DC power 506 can track input DC power 110 (e.g., ratiometrically, with a fixed voltage offset, etc.). Put another way, capacitor 608 may be an output reservoir capacitor coupled between output DC power node 614 and ground and may be configured (e.g., in combination with resistor 606) to hold the second variable voltage level of regulated DC power 506 steady with respect to a first timescale associated with a data rate of a digital data signal (e.g., digital data signal 112), and to allow the second variable voltage level of regulated DC power 506 to vary with respect to a second timescale at least one hundred times longer than the first timescale (e.g., the timescale at which input DC power 110 is changing, as described above in relation to FIGS. 3A and 3B). It will be understood that other resistors and/or capacitors may be used elsewhere in hybrid linear regulator circuit and/or other circuits described herein for the same or similar purposes as may serve a particular implementation.

Like FIG. 6, FIG. 7 shows an exemplary implementation of hybrid linear regulator circuit 502 of ASK modulation controller 402. The implementation of FIG. 7 is similar to the implementation of FIG. 6, but FIG. 7 illustrates more specific details of a particular implementation of driver circuits 604. Specifically, as shown, high-voltage driver circuit 604-1 includes a p-type transistor 702-p while low-voltage driver circuit 604-2 includes an n-type transistor 702-n.

Transistors 702 (i.e., p-type transistor 702-p and n-type transistor 702-n) may be implemented by any suitable transistor or other device configured to perform the operations described herein. For example, p-type transistor 702-p may be a p-channel field effect transistor ("FET") (i.e., a p-channel metal oxide semiconductor ("PMOS") transistor or p-channel metal oxide semiconductor field effect transistor ("p-channel MOSFET")) having a gate terminal coupled with a control signal 704-1 (i.e., a first control signal based on reference signal 512 and feedback from regulated DC power 506 as will be described below), a source terminal coupled with input DC power 110, and a drain terminal coupled with regulated DC power 506. Similarly, n-type transistor 702-n may be an n-channel FET (i.e., an n-channel metal oxide semiconductor ("NMOS") transistor or an n-channel MOSFET) having a gate terminal coupled with a control signal 704-2 (i.e., a second control signal based on reference signal 512 and the feedback from regulated DC power 506 as will be described below), a source terminal coupled with regulated DC power 506, and a drain terminal coupled with input DC power 110.

As another example, p-type transistor 702-p may be a PNP bipolar transistor (e.g., a PNP bipolar junction transistor ("BJT") or the like) having a base terminal coupled with control signal 704-1, an emitter terminal coupled with input DC power 110, and a collector terminal coupled with regulated DC power 506. Similarly, n-type transistor 702-*n* may be an NPN bipolar transistor (e.g., a NPN BJT or the like) having a base terminal coupled with control signal 704-2, an emitter terminal coupled with regulated DC power 506, and a collector terminal coupled with input DC power 110.

Regardless of how transistors 702 are implemented (e.g., by FETs, bipolar transistors, or by some other suitable device), p-type transistor 702-*p* may apply, to input DC power 110 in accordance with control signal 704-1, a first step-down resistance to step down input DC power 110 (i.e., which is at the first variable voltage level) to drive regulated DC power 506 at the second variable voltage level. In particular, as described above, p-type transistor 702-*p* may apply the first step-down resistance to step down input DC power 110 to drive regulated DC power 506 when the first variable voltage level of input DC power 110 is greater than the first threshold voltage level.

For example, in one implementation p-type transistor 702-*p* may be implemented by a PMOS transistor with a gate coupled to control signal 704-1, a source coupled to input DC power 110, and a drain coupled to regulated DC power 506. Additionally, high-voltage driver stage 604-1 may include a first control component powered by auxiliary DC power 602 and that controls the driving of regulated DC power 506 at output DC power node 614 based on reference signal 512 and the feedback from regulated DC power 506 when the first variable voltage level of input DC power 110 is greater than the first threshold voltage level. More specifically, as shown in FIG. 7, the first control component may be implemented by a differential amplifier 706-1 included within high-voltage driver stage 604-1.

Differential amplifier 706-1 may derive control signal 704-1 from reference signal 512 and from the feedback from regulated DC power 506 by amplifying a positive voltage difference between regulated DC power 506 and reference signal 512. In other words, as shown, regulated DC power 506 may be coupled to a non-inverting terminal of differential amplifier 706-1 (i.e., indicated by a positive (+) sign) while reference signal 512 may be coupled to an inverting terminal of differential amplifier 706-1 (i.e., indicated by a negative (−) sign). In this way, differential amplifier 706-1 may amplify the positive voltage difference between regulated DC power 506 and reference signal 512 (i.e., the voltage level of regulated DC power 506 minus the voltage level of reference signal 512). Differential amplifier 706-1 may tend to drive control signal 704-1 to a steady state in which both regulated DC power 506 and reference signal 512 are at the same voltage level (i.e., the second variable voltage level). Specifically, differential amplifier 706-1 may drive control signal 704-1 to cause a gate-source voltage between the gate and the source of p-channel transistor 702-*p* to be just large enough to cause p-channel transistor 702-*p* (e.g., operating in a linear region of the transistor also known as an "ohmic mode" or a "triode mode") to apply the first step-down resistance such that input DC power 110 is stepped down to drive regulated DC power 506 at the same voltage as reference signal 512 (i.e., the second variable voltage level).

High-voltage driver stage 604-1 (i.e., differential amplifier 706-1 and p-channel transistor 702-*p*) may be well suited for driving regulated DC power 506 when the first variable voltage level (i.e., the voltage level of input DC power 110) is relatively high. For example, if the first variable voltage level is 3.0 V and the threshold voltage of p-channel transistor 702-*p* (e.g., the minimum gate-source voltage needed to put p-channel transistor 702-*p* into the linear region where p-channel transistor 702-*p* will apply the first step-down resistance) is 0.7 V, differential amplifier 706-1 may need to drive control signal 704-1 to approximately 2.3 V (i.e., 3.0 V−0.7 V) for p-channel transistor 702-*p* to enter the linear region and apply the proper step-down resistance to drive regulated DC power 506. This may be well within the operating parameters of differential amplifier 706-1 and p-channel transistor 702-*p* such that high-voltage driver stage 604-1 may adequately drive regulated DC power 506 by itself.

However, high-voltage driver stage 604-1 may not be well suited for driving regulated DC power 506 when the first variable voltage level is relatively low. For example, if the first variable voltage level is 0.6 V and the threshold voltage of p-channel transistor 702-*p* is 0.7 V, differential amplifier 706-1 may need to drive control signal 704-1 below 0 V (i.e., to 0.6 V−0.7 V=−0.1 V) for p-channel transistor 702-*p* to enter the linear region and apply the proper step-down resistance to drive regulated DC power 506. This may be problematic for differential amplifier 706-1 to do and/or may be outside of the typical operating parameters of p-channel transistor 702-*p* such that high-voltage driver stage 604-1 may be inadequate to drive regulated DC power 506 by itself (or at all) in this case.

Referring now to low-voltage driver stage 604-2, n-type transistor 702-*n* may apply, to input DC power 110 in accordance with control signal 704-2, a second step-down resistance to step down input DC power 110 to drive regulated DC power 506 at the second variable voltage level. In particular, as described above, n-type transistor 702-*n* may apply the second step-down resistance to step down input DC power 110 to drive regulated DC power 506 when the first variable voltage level of input DC power 110 is less than the second threshold voltage level. As will be described in more detail below, low-voltage driver stage 604-2 may drive regulated DC power 506 mutually with or in parallel with high-voltage driver stage 604-1. In other words, both driver stages 604 may share the task of driving regulated DC power 506, each contributing in accordance with how well suited it is to step down input DC power 110 at the first variable voltage level.

As an example, in one implementation n-type transistor 702-*n* may be implemented by a NMOS transistor with a gate coupled to control signal 704-2, a source coupled to regulated DC power 506, and a drain coupled to input DC power 110. Additionally, low-voltage driver stage 604-2 may include a second control component powered by auxiliary DC power 602 and that controls the driving of regulated DC power 506 at output DC power node 614 based on reference signal 512 and feedback from regulated DC power 506 when the first variable voltage level of input DC power 110 is less than the second threshold voltage level. More specifically, as shown in FIG. 7, the second control component may be implemented by a differential amplifier 706-2 included within low-voltage driver stage 604-2.

Differential amplifier 706-2 may derive control signal 704-2 from reference signal 512 and from the feedback from regulated DC power 506 by amplifying a negative voltage difference between regulated DC power 506 and reference signal 512. In other words, as shown, regulated DC power 506 may be coupled to an inverting terminal of differential amplifier 706-2 (i.e., indicated by a negative (−) sign) while reference signal 512 may be coupled to a non-inverting terminal of differential amplifier 706-2 (i.e., indicated by a positive (+) sign). In this way, differential amplifier 706-2 may amplify the negative voltage difference between regulated DC power 506 and reference signal 512 (i.e., the voltage level of reference signal 512 minus the voltage level of regulated DC power 506). Differential amplifier 706-2 may tend to drive control signal 704-2 to a steady state in which both regulated DC power 506 and reference signal 512 are at the same voltage level (i.e., the second variable voltage level). Specifically, differential amplifier 706-2 may drive control signal 704-2 to cause a gate-source voltage between the gate and the source of n-channel transistor 702-n to be just large enough to cause n-channel transistor 702-n (e.g., operating in a linear region of the transistor) to apply the second step-down resistance such that input DC power 110 is stepped down to drive regulated DC power 506 at the same voltage as reference signal 512 (i.e., the second variable voltage level).

Low-voltage driver stage 604-2 (i.e., differential amplifier 706-2 and n-channel transistor 702-n) may be well suited for driving regulated DC power 506 when the first variable voltage level (i.e., the voltage level of input DC power 110) is relatively low. For example, if the first variable voltage level is 0.6 V and the threshold voltage of n-channel transistor 702-n (e.g., the minimum gate-source voltage needed to put n-channel transistor 702-n into the linear region where n-channel transistor 702-n will apply the first step-down resistance) is 0.7 V, differential amplifier 706-2 may need to drive control signal 704-1 to approximately 1.3 V (i.e., 0.6 V+0.7 V) for n-channel transistor 702-n to enter the linear region and apply the proper step-down resistance to drive regulated DC power 506. This may be well within the operating parameters of differential amplifier 706-1 and n-channel transistor 702-n such that low-voltage driver stage 604-2 may adequately drive regulated DC power 506 by itself.

However, low-voltage driver stage 604-2 may not be well suited for driving regulated DC power 506 when the first variable voltage level is relatively high. For example, if the first variable voltage level is 3.0 V and the threshold voltage of n-channel transistor 702-n is 0.7 V, differential amplifier 706-2 may need to drive control signal 704-2 to approximately 3.7 V (i.e., 3.0 V+0.7 V) for n-channel transistor 702-n to enter the linear region and apply the proper step-down resistance to drive regulated DC power 506. This may be problematic for differential amplifier 706-2 to do (e.g., because this voltage level is outside of the operating range of differential amplifier 706-2 and/or above auxiliary DC power 602 powering differential amplifier 706-2) and/or may be outside of the operating parameters of n-channel transistor 702-n such that low-voltage driver stage 604-2 may be inadequate to drive regulated DC power 506 by itself (or at all) in this case.

As described above, while transistors 702 are shown to be FETs in FIG. 7, transistors 702 may be implemented by any transistors as may serve a particular implementation. Similarly, while the first and second control components shown in FIG. 7 to be driving control signals 704 (i.e., control signals 704-1 and 704-2) are differential amplifiers 706 (i.e., differential amplifiers 706-1 and 706-2), it will be understood that the first and second control components may be implemented in any manner as may serve a particular implementation. For example, rather than differential amplifiers (e.g., operational amplifiers, error amplifiers, etc.), the control components may be implemented by, for example, a charge pump and a voltage comparator, or in another suitable manner.

As described above, high-voltage driver stage 604-1 and low-voltage driver stage 604-2 may complement one another in that high-voltage driver stage 604-1 may be better suited to driving regulated DC power 506 when the first variable voltage level of input DC power 110 is relatively high while low-voltage driver stage 604-2 may be better suited to driving regulated DC power 506 when the first variable voltage level is relatively low. However, one advantage of hybrid linear regulator circuit 502 may be that, when the first variable voltage level is neither particularly high nor low (e.g., when the first variable voltage level is less than the first threshold voltage level and greater than the second threshold voltage level), high-voltage driver stage 604-1 and low-voltage driver stage 604-2 may be configured to mutually (e.g., cooperatively) drive regulated DC power 506 at output DC power node 614. Thus, as the first variable voltage level varies throughout the voltage range (e.g., as shown above in FIG. 3B), regulated DC power 506 may be continually and smoothly driven by either or both of driver stages 604 without any interruption as one driver stage 604 reaches its limits and the other reaches its prime operating region.

Returning to FIG. 5, hybrid linear regulator circuit 502 may provide regulated DC power 506 to intermediate DC power switching circuit 504, which may generate intermediate DC power 404. Intermediate DC power 404 may be referred to herein as a toggled output DC power because intermediate DC power 404 may toggle between output DC power 110 (i.e., at the first voltage level) and regulated DC power 506 (i.e., at the second voltage level tracking the first voltage level). As shown, ASK modulation controller 402 may include a toggled output DC power node by way of which system ASK modulation controller 402 provides intermediate DC power 404 (i.e., toggled output DC power) that toggles between the first and the second variable voltage levels in accordance with digital data signal 112.

Figure 8:
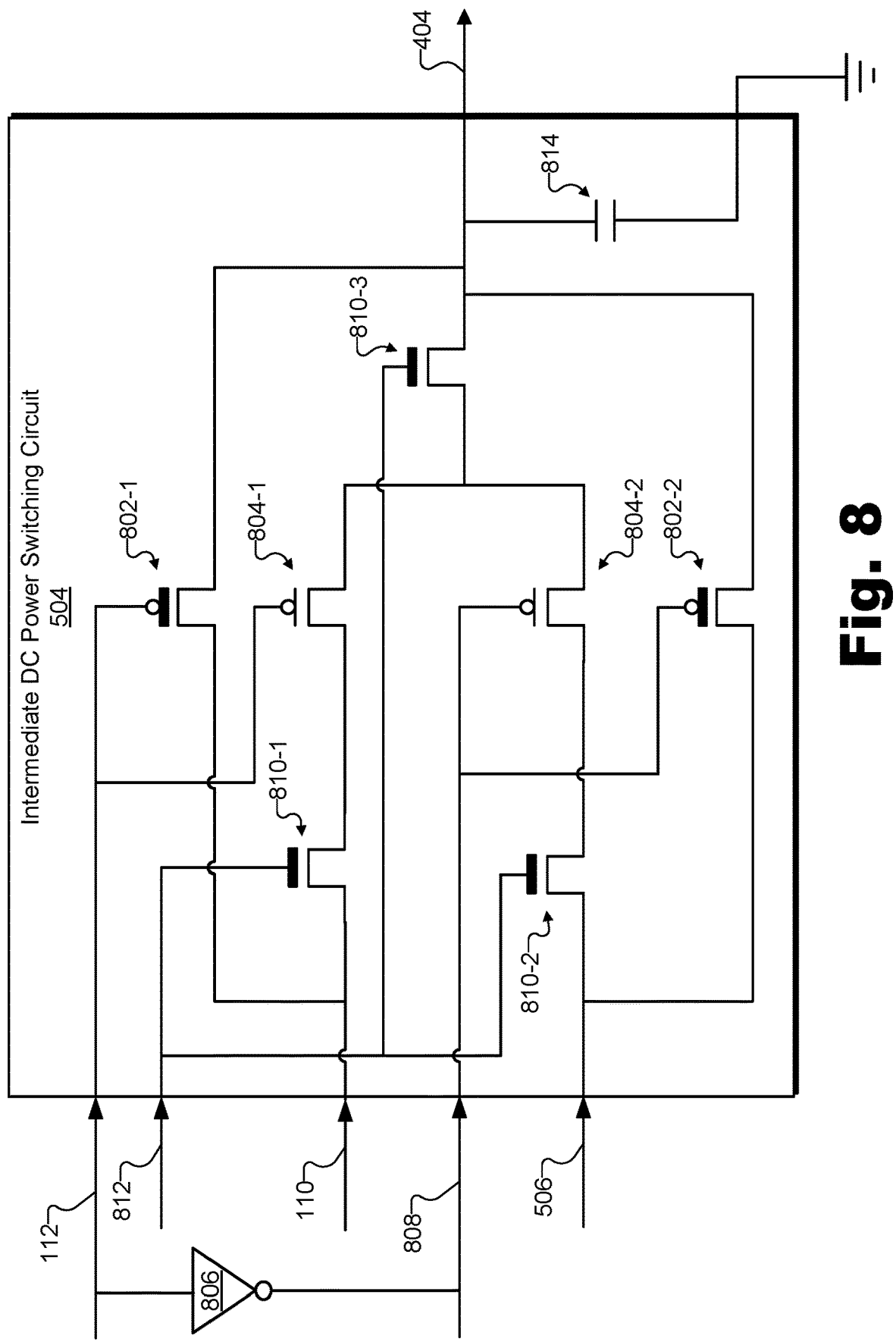
FIG. 8 illustrates an exemplary implementation of an intermediate direct current ("DC") power switching circuit of the ASK modulation controller of FIG. 5 according to principles described herein.

FIG. 8 illustrates an exemplary implementation of intermediate DC power switching circuit 504 that generates intermediate DC power 404. The implementation of intermediate DC power switching circuit 504 in FIG. 8 shows a high-voltage switching stage coupled between the input and output DC power nodes (i.e., the terminals of intermediate DC power switching circuit 504 to which input DC power 110 and regulated DC power 506 are coupled) and the toggled output DC power node (i.e., the terminal of intermediate DC power switching circuit to which intermediate DC power 404 is coupled). More specifically, the high-voltage switching stage includes two transistors 802 (i.e., transistors 802-1 and 802-2), which may be implemented by p-channel FETs or other suitable transistors. The high-voltage switching stage (i.e., transistors 802) may be configured to drive intermediate DC power 404 at the toggled output DC power node when the first variable voltage level of the input DC power is greater than a third threshold voltage level. For example, the high-voltage switching stage may switch, in accordance with digital data signal 112, between coupling the toggled output DC power node with input DC power 100 and coupling the toggled output DC power node with regulated DC power 506.

Similarly, the implementation of intermediate DC power switching circuit 504 in FIG. 8 shows a low-voltage switching stage coupled between the input and output DC power nodes and the toggled output DC power node. More specifically, the low-voltage switching stage includes two transistors 804 (i.e., transistors 804-1 and 804-2), which may be implemented by p-channel FETs or other suitable transistors. The low-voltage switching stage (i.e., transistors 804) may be configured to drive intermediate DC power 404 at the toggled output DC power node when the first variable voltage level of the input DC power is less than the third threshold voltage level. For example, like the high-voltage switching stage, the low-voltage switching stage may switch, in accordance with digital data signal 112, between coupling the toggled output DC power node with input DC power 100 and coupling the toggled output DC power node with regulated DC power 506.

Intermediate DC power switching circuit 504 includes two different switching stages (i.e., the high-voltage and the low-voltage switching stages) to accommodate the fact that the first variable voltage level of input DC power 110 (as well as the second variable voltage level of regulated DC power 506) may be varying throughout a relatively wide range (e.g., between, for example, 0.6 V and 3.0 V). For example, transistors 802 may be thick-oxide transistors (i.e., transistors with a relatively thick layer of oxide or dielectric material in between the gate and the silicon beneath the gate) configured to operate optimally at relatively high voltage levels. As shown, thick-oxide transistors are illustrated in FIG. 8 as having thicker gates than thin-oxide transistors; however, it will be understood that the oxide in such transistors may be relatively thick, rather than the gates themselves. At voltage levels greater than the third threshold voltage level (e.g., a midpoint of the voltage range throughout which the first variable voltage level varies or the like), for example, the thick-oxide transistors may operate responsively and without being damaged, while, at voltage levels less than the third threshold voltage level, the thick-oxide transistors may be less responsive and/or may otherwise fail to operate optimally or at all. Similarly, transistors 804 may be thin-oxide transistors (i.e., transistors with a relatively thin layer of oxide or dielectric material in between the gate and the silicon beneath the gate) configured to operate optimally at relatively low voltage levels. As shown, thin-oxide transistors are illustrated in FIG. 8 as having thinner gates than thick-oxide transistors; however, it will be understood that the oxide in such transistors may be relatively thin, rather than the gates themselves. At voltage levels less than the third threshold voltage level, for example, the thin-oxide transistors may operate responsively and without being damaged, while, at voltage levels greater than the third threshold voltage level, the thin-oxide transistors may be damaged or may otherwise fail to operate optimally or at all.

Various versions of digital data signal 112 may be used in intermediate DC power switching circuit 504. For example, as shown, a non-inverted version of digital data signal 112 may be coupled to the gates of transistors 802-1 and 804-1. In some examples, digital data signal 112 may be provided only to one of transistors 802-1 and 804-1 (e.g., depending on whether the first variable voltage level is greater than or less than the third threshold voltage level). Digital data signal 112 may also be inverted by an inverter 806 to generate an inverted version 808 of digital data signal 112 that may be coupled to the gates of transistors 802-2 and 804-2. Again, in certain examples, version 808 of digital data signal 112 may be provided only to one of transistors 802-2 and 804-2 (e.g., dependent on the first variable voltage level).

As such, when digital data signal 112 is at a voltage level representative of a first binary value (e.g., when digital data signal 112 represents a binary '0'), the respective gates of transistors 802-1 and/or 804-1 may be driven so as to effectively couple input DC power 110 with the toggled DC output node (i.e., to drive intermediate DC power 404 to be the same as input DC power 110) regardless of whether the first variable voltage level is greater or less than the third threshold voltage level. At the same time, inverted version 808 of digital data signal 112 is at a voltage level representative of a second binary value opposite to the first binary value (e.g., representing a binary '1'). Thus, the respective gates of transistors 802-2 and 804-2 may each be driven so as to block regulated DC power 506 from being coupled with the toggled DC output node regardless of whether the first variable voltage level is greater or less than the third threshold voltage level. Then, when digital data signal 112 toggles (e.g., so that digital data signal 112 represents a binary '1' and inverted version 808 represents a binary '0'), transistors 802 and/or 804 may toggle to effectively couple regulated DC power 506 to the toggled DC output node in place of input DC power 110 (i.e., blocking input DC power 110 from being coupled to the toggled DC output node).

Inverter 806 may be implemented in any way as may serve a particular implementation. For example, as shown, inverter 806 may be implemented as a simple inverter. In other examples, inverted version 808 of digital data signal 112 may be generated in other ways that provide more control over when inverted version 808 toggles with respect to the toggling of digital data signal 112. For example, in certain examples, version 808 may be made to toggle slightly before or slightly after digital data signal 112 toggles so as to guarantee the toggled DC output node is always driven and never "floats" for any length of time even during the transition from being coupled to input DC power 110 to being coupled to regulated DC power 506.

Additional transistors 810 (i.e., transistors 810-1, 810-2, and 810-3) may be placed surrounding thin-oxide transistors 804. Transistors 810 may be thick-oxide transistors (e.g., n-channel FETs or other suitable transistors) configured to isolate thin-oxide transistors 804 from voltages that may cause thin-oxide transistors 804 to be damaged when such voltages are present. For example, if the voltage range throughout which input DC power 110 dynamically varies is 0.6-3.0 V, the third threshold voltage level (i.e., the threshold voltage level above which the high-voltage switching stage is to be used rather than the low-voltage switching stage) may be 2.0 V. A voltage detector (e.g., within intermediate DC power switching circuit 504 or elsewhere within ASK modulation system 400) may detect that the first variable voltage level of input DC power 110 exceeds 2.0 V and, in response, may generate an enable signal 812 to drive the gates of transistors 810 to cause transistors 810 to isolate the low-voltage switching stage (i.e., transistors 804) from input DC power 110, regulated DC power 506, and intermediate DC power 404. Then, when the voltage detector detects that the first variable voltage level of input DC power 110 is less than 2.0 V, enable signal 812 may be generated to drive the gates of transistors 810 to cause transistors 810 to couple the low-voltage switching stage to input DC power 110, regulated DC power 506, and intermediate DC power 404.

Accordingly, in some examples, the low-voltage switching stage may include a first thin-oxide FET (e.g., transistor 804-1) configured to operate at voltage levels less than the third threshold voltage level and a first thick-oxide FET (e.g., transistor 810-1) coupled between the first thin-oxide FET and the input DC power node (e.g., configured to isolate the first thin-oxide FET from input DC power 110 when the first variable voltage level is greater than the third threshold voltage level). The low-voltage switching stage may also include a second thin-oxide FET (e.g., transistor 804-2) configured to operate at voltage levels less than the third threshold voltage level and a second thick-oxide FET (e.g., transistor 810-2) coupled between the second thin-oxide FET and the output DC power node (e.g., configured to isolate the second thin-oxide FET from regulated DC power 506 when the first variable voltage level is greater than the third threshold voltage level). Additionally, the low-voltage switching stage may further include a third thick-oxide FET (e.g., transistor 810-3) coupled between the first and second thin-oxide FETs (e.g., coupled to both transistors 804) and the toggled output DC power node (e.g., configured to isolate the first and second thin-oxide FETs from intermediate DC power 404 when the first variable voltage level is greater than the third threshold voltage level).

As shown, a capacitor 814 may be coupled between the toggled output DC power node and ground. Capacitor 814 may be selected to be large enough to filter the carrier frequency from RF driver 104 (which may be powered by intermediate DC power 404), while being small enough to allow the voltage level of intermediate DC power 404 to responsively switch between the first variable voltage level and the second variable voltage level as intermediate DC power switching circuit 504 performs the switching in accordance with digital data signal 112. Thus, for example, capacitor 814 may be relatively small (e.g., 10-20 nanofarads) such that capacitor 814 may filter at the RF carrier frequency of RF driver 104 (e.g., approximately 49 MHz in some examples) while being responsive at the data rate of digital data signal 112 (e.g., approximately 1 MHz in some examples).

Returning to FIG. 5, modulation depth control circuit 508 may receive input DC power 110 at the first voltage level (e.g., a variable voltage level in certain examples), as well as modulation depth select signal 510 representative of a particular ASK modulation depth in a plurality of ASK modulation depths supported by modulation depth control circuit 508. Based on modulation depth select signal 510 and the first voltage level of input DC power 110, modulation depth control circuit 508 may generate reference signal 512 at the second voltage level tracking the first voltage level.

In some examples, the particular ASK modulation depth represented by modulation depth select signal 510 may not be more than 20% modulation depth. For instance, as will be described below in more detail, such a small modulation depth may provide more efficiency to ASK modulation system 400 and help transmit as much RF power as possible for a given first voltage level. As one example, the voltage level of input DC power 110 may be 3.0 V and modulation depth select signal 510 may represent a 10% modulation depth. In this example, modulation depth control circuit 508 may generate reference signal 512 to be 2.7 V (i.e., 10% less than 3.0 V). Then, for instance, if the voltage level of input DC power 110 later decreases to 2.0 V (e.g., while modulation depth select signal 510 remains unchanged), modulation depth 508 may generate reference signal 512 to be 1.8 V (i.e., 10% less than 2.0 V).

In other examples, the particular ASK modulation depth represented by modulation depth select signal 510 may be 100% modulation depth. While 100% modulation depth may be less efficient and/or facilitate less RF power transmission than smaller modulation depths described herein (e.g., the modulation depth that is no more than 20% modulation depth described above), it may be desirable that modulation depth control circuit 508 support a 100% modulation depth option for certain purposes. For example, by supporting a 100% modulation depth option, modulation depth control circuit 508 may be compatible with load circuitry (e.g., legacy load circuitry) that is configured to receive on-off keying modulated (i.e., 100% modulation depth ASK modulated) RF data such as illustrated by segment 116-A of RF output power 116 in FIG. 3A. It will also be understood that other suitable ways (e.g., more efficient ways) of achieving 100% modulation depth may be employed in certain implementations. For example, instead of outputting reference signal 512 as a 0 V ground signal, both modulation depth control circuit 508 and hybrid linear regulator circuit 502 may be bypassed (e.g., through a combination of switches, signal configurations, etc.) to revert to a configuration such as the implementation of modulation system 100 illustrated in FIG. 1.

Figure 9:
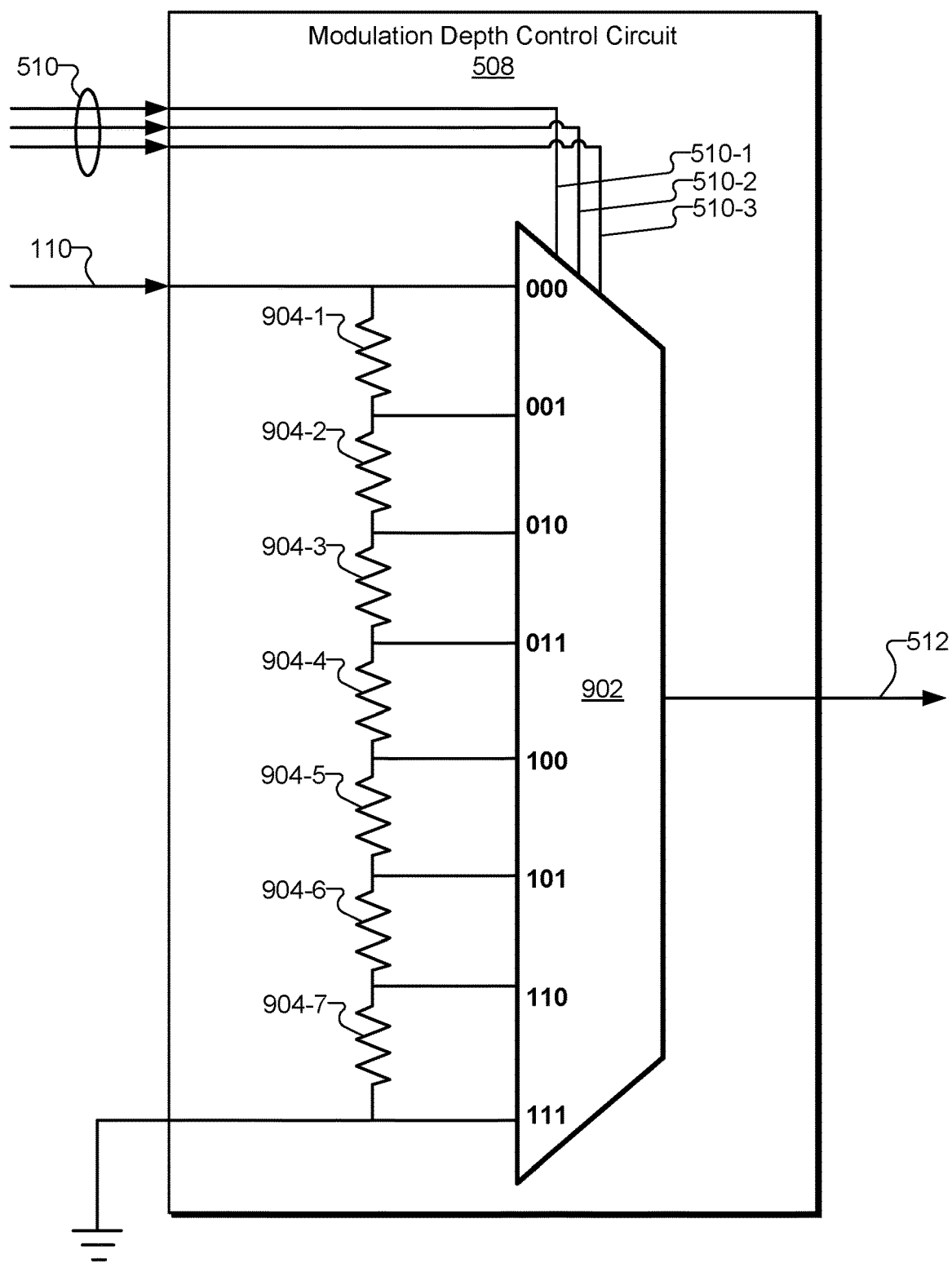
FIG. 9 illustrates an exemplary implementation of a modulation depth control circuit of the ASK modulation controller of FIG. 5 according to principles described herein.

Modulation depth control circuit 508 may be implemented in any manner as may serve a particular implementation. For example, FIG. 9 illustrates an exemplary implementation of modulation depth control circuit 508. Specifically, as shown, the implementation of modulation depth control circuit 508 in FIG. 9 includes circuitry implementing a multiplexer 902 with a plurality of signal inputs (i.e., labeled "000", "001", "010", "011", "100", "101", "110", "111"), at least one selection input (i.e., coupled to modulation depth select signal 510), and a signal output (i.e., coupled to reference signal 512). As further shown in FIG. 9, modulation depth control circuit 508 may also include circuitry implementing a resistor ladder composed of resistors 904 (i.e., resistors 904-1 through 904-7) and that divides the first voltage level of input DC power 110 into a plurality of potential reference signals tracking (e.g., following ratiometrically) the first voltage level and no greater than the first voltage level.

As shown, in the example of FIG. 9, each of the potential reference signals tapped from between resistors 904 may be coupled with a respective signal input in the plurality of signal inputs of multiplexer 902. Depending on the values of resistors 904, which may have equal or different resistances as may serve a particular implementation, each of the potential reference signals may have different voltage levels tracking (e.g., ratiometric with) the first voltage level of input DC power 110. For instance, if all of resistors 904 are equal, the potential reference signal may have voltage levels of 100% of the first voltage level (i.e., for the signal coupled to the signal input labeled "000"), approximately 85.7% of the first voltage level (i.e., for the signal coupled to the signal input labeled "001"), approximately 71.4% of the first voltage level (i.e., for the signal coupled to the signal input labeled "010"), approximately 57.1% of the first voltage level (i.e., for the signal coupled to the signal input labeled "011"), approximately 42.8% of the first voltage level (i.e., for the signal coupled to the signal input labeled "100"), approximately 28.5% of the first voltage level (i.e., for the signal coupled to the signal input labeled "101"), approximately 14.2% of the first voltage level (i.e., for the signal coupled to the signal input labeled "110"), and 0% of the first voltage level (i.e., for the signal coupled to the signal input labeled "111").

In other examples having more or fewer resistors 904 or resistors having different values, other percentages between 0% and 100% of the first voltage level may be implemented. For example, resistors 904 may be selected to provide potential reference signals with voltage levels of 100%, 90%, 80%, and 70% of the first voltage level.

Modulation depth select signal 510 may be a digital signal that is coupled with the at least one selection input of multiplexer 902. As shown in FIG. 9, for example, modulation depth select signal 510 may be a multiple-bit digital signal (e.g., including three signals 510-1, 510-2, and 510-3) that is coupled to three selection inputs of multiplexer 902 to select from the potential reference signals coming in to selection inputs "000" through "111". For instance, if modulation depth select signal 510 is representative of "001" (i.e., signal 510-1 is '0', signal 510-2 is '0', and signal 510-3 is '1'), multiplexer 902 may select the potential reference signal tapped from between resistors 904-1 and 904-2 (i.e., 85.7% of the first voltage level in the example above) and to output it as reference signal 512. In other words, whichever of the potential reference signals is selected may become reference signal 512 at the second voltage level tracking the first voltage level of input DC power 110.

In other examples, modulation depth control circuit 508 may be implemented in other manners. For example, another implementation of modulation depth control circuit 508 may include circuitry implementing a variable resistor with a signal input, a selection input, and a signal output. In this implementation, input DC power 110 (i.e., at the first voltage level) may be coupled with the signal input, modulation depth select signal 510 may be an analog signal coupled to the selection input, and the signal output may be the reference signal 512 generated at the second voltage level.

In some examples, modulation depth control circuit 508 may be configured to remain constant under most circumstances. For example, a particular implementation of ASK modulation system 400 may be configured to operate with a modulation depth of, for instance, 14.3% (i.e., corresponding to a second voltage level of 85.7% of the first voltage level) and modulation depth select signal 510 may be set accordingly (e.g., to "001") by the manufacturer to rarely (if ever) be changed. In a cochlear implant context, for example, modulation depth select signal 510 may be manually altered (e.g., by a clinician) so as to be optimized for a particular cochlear implant (e.g., a model configured to receive RF power ASK modulated at 14.3% modulation depth, a legacy model configured to receive RF power ASK modulated at 100%, etc.), but may not be user configurable so that the patient does not accidentally change the modulation depth to a sub-optimal modulation depth (e.g., a modulation depth that is inefficient or does not allow the cochlear implant to receive sufficient RF power).

In certain examples, modulation depth select signal 510 may also be automatically altered to switch from one modulation depth to a different modulation depth. For example, modulation depth select signal 510 may be automatically altered so as to change an amount of RF output power that is to be delivered to the load. Some load circuitry may vary in how much RF power is drawn. For example, a cochlear implant load may require more RF power when sounds presented to a patient are louder than when sounds presented to the patient are quieter. Accordingly, as an alternative to setting the RF power level at a high enough level to always provide whatever power is used (which may be inefficient and detrimental to aspects of the system such as battery life, heat generation, etc.), the system may track how much power is to be used (e.g., by tracking the volume of sound in the cochlear implant load example) and, based on the tracking, modulation depth select signal 510 may be dynamically and automatically altered to efficiently provide only the approximate amount of power that is to actually be used by the load. For example, modulation depth select signal 510 may select a lower modulation depth (e.g., 14.3%) when RF power being used by a load is normal or relatively high, but may be automatically changed to a higher modulation depth (e.g., 28.6%, corresponding to a second voltage level of 71.4% of the first voltage level) when RF power being used by the load is relatively low.

With each of the various components and subcomponents of ASK modulation system 400 described, an example will now be shown to illustrate ASK modulation system 400 in operation.

FIGS. 10A-10B show exemplary waveforms associated with the ASK modulation of digital data signal 112 onto RF power 406. More specifically, FIG. 10A illustrates the modulation on a relatively short timescale (e.g., in microseconds), while FIG. 10B illustrates the modulation on a relatively long timescale (e.g., in milliseconds). In some examples, certain features illustrated in FIG. 10B may take place over a timescale several (e.g., three or more) orders of magnitude greater than a timescale over which certain features illustrated in FIG. 10A may take place.

Like FIG. 3A described above, FIG. 10A shows segment 112-A of digital data signal 112 and segment 110-A of input DC power 110. Unlike FIG. 3A, however, FIG. 10A also illustrates a relatively short segment 506-A of regulated DC power 506 (e.g., generated by hybrid linear regulator circuit 502 as described above) on the same graph as segment 110-A. Additionally, FIG. 10A shows a relatively short segment 404-A of intermediate DC power 404, which is also generated within ASK modulation system 400 (e.g., by intermediate DC power switching circuit 504). Segment 404-A shows how intermediate DC power switching circuit 504 switches between the first voltage level of input DC power 110 and the second voltage level of regulated DC power 506 in accordance with digital data signal 112.

Powered by intermediate DC power 404, RF driver circuit 104 may generate and transmit RF output power 406, a segment 406-A of which is illustrated in FIG. 10A. The length (in terms of time) of segment 406-A of RF output power 406 may be the same as the lengths of segments 112-A, 110-A, 506-A, and 404-A. Accordingly, as shown, segment 406-A may include periods of approximately one to two microseconds each where RF output power is being transmitted at 100% (i.e., at a voltage corresponding to the first voltage level of input DC power 110) and at an RF carrier frequency (e.g., 49 MHz or another frequency corresponding to a period significantly shorter than the data period of one to two microseconds) to represent, for example, a binary '1'. Rather than periods where no RF power is transmitted (as shown in FIG. 3A), however, FIG. 10A may include periods where RF output power is being transmitted at, for example, 90% to represent a binary '0'. As such, segment 406-A shows how RF output power 406 may deliver wireless power to the load that is representative of digital data signal 112 and that includes significantly more power than RF output power 116 provided by modulation system 100 (see FIG. 3A). Specifically, rather than only transmitting power about half of the time, RF output power 406 continually delivers nearly 100% (e.g., either 100% or 90%) all the time.

Like FIG. 3B described above, FIG. 10B shows segment 112-B of digital data signal 112 and segment 110-B of input DC power 110. Unlike FIG. 3B, however, FIG. 10B also illustrates a relatively long segment 506-B of regulated DC power 506 on the same graph as segment 110-B. Additionally, FIG. 10B shows a relatively long segment 404-B of intermediate DC power 404. Segment 404-B shows how intermediate DC power switching circuit 504 switches between the first voltage level of input DC power 110 and the second voltage level of regulated DC power 506 in accordance with digital data signal 112 over a long period of time. Digital data signal 112, input DC power 110, regulated DC power 506, and intermediate DC power 404 may be changing at the same rates as illustrated in FIG. 10A. However, because of the relatively long timescale represented in FIG. 10B, the signals may be much more compressed as compared to the waveforms of FIG. 10A. The timescales shown in FIGS. 10A and 10B are related with the timescales shown in FIGS. 3A and 3B, respectively.

Segment 406-B shows a segment of RF output power 406 with the same length (in terms of time) as the lengths of segments 112-B, 110-B, 506-B, and 404-B. Accordingly, as shown, segment 406-B may include periods of approximately one to two microseconds each where RF output power is being transmitted at 100% (i.e., at a voltage corresponding to the first voltage level of input DC power 110) and at an RF carrier frequency (e.g., 49 MHz or another frequency corresponding to a period much shorter than the one to two microsecond data period) to represent, for example, a binary '1'. Rather than periods where no RF power is transmitted, as shown in FIG. 3A, however, FIG. 10B may include periods where RF output power is being transmitted at, for example, 90% to represent a binary '0'. However, because of the relatively long timescale, such toggling cannot be seen in segment 406-B. Segment 116-B does illustrate, however, that RF output power 406 may increase (i.e., provide power at larger and larger voltage levels) and diminish (i.e., provide power at smaller and smaller voltage levels) in accordance with the changing of input DC power 110 illustrated by segment 110-B. As such, segment 406-B shows how RF output power 406 may deliver differing amounts of wireless power to the load based on what the load may require (i.e., based on a power delivery parameter).

As described above (and as made apparent by, for example, contrasting segment 116-A of RF output power 116 shown in FIG. 3A and segment 406-A of RF output power 406 shown in FIG. 10A), significantly more power may be transmitted for a given first voltage level using ASK modulation with a low modulation depth (e.g., as performed by ASK modulation system 400) than using ASK modulation with 100% modulation depth (i.e., on-off keying modulation as performed by modulation system 100). As such, ASK modulation system 400 may be just as efficient or more efficient than modulation system 100 while delivering significantly more wireless power for a given first voltage level.

Figure 11:
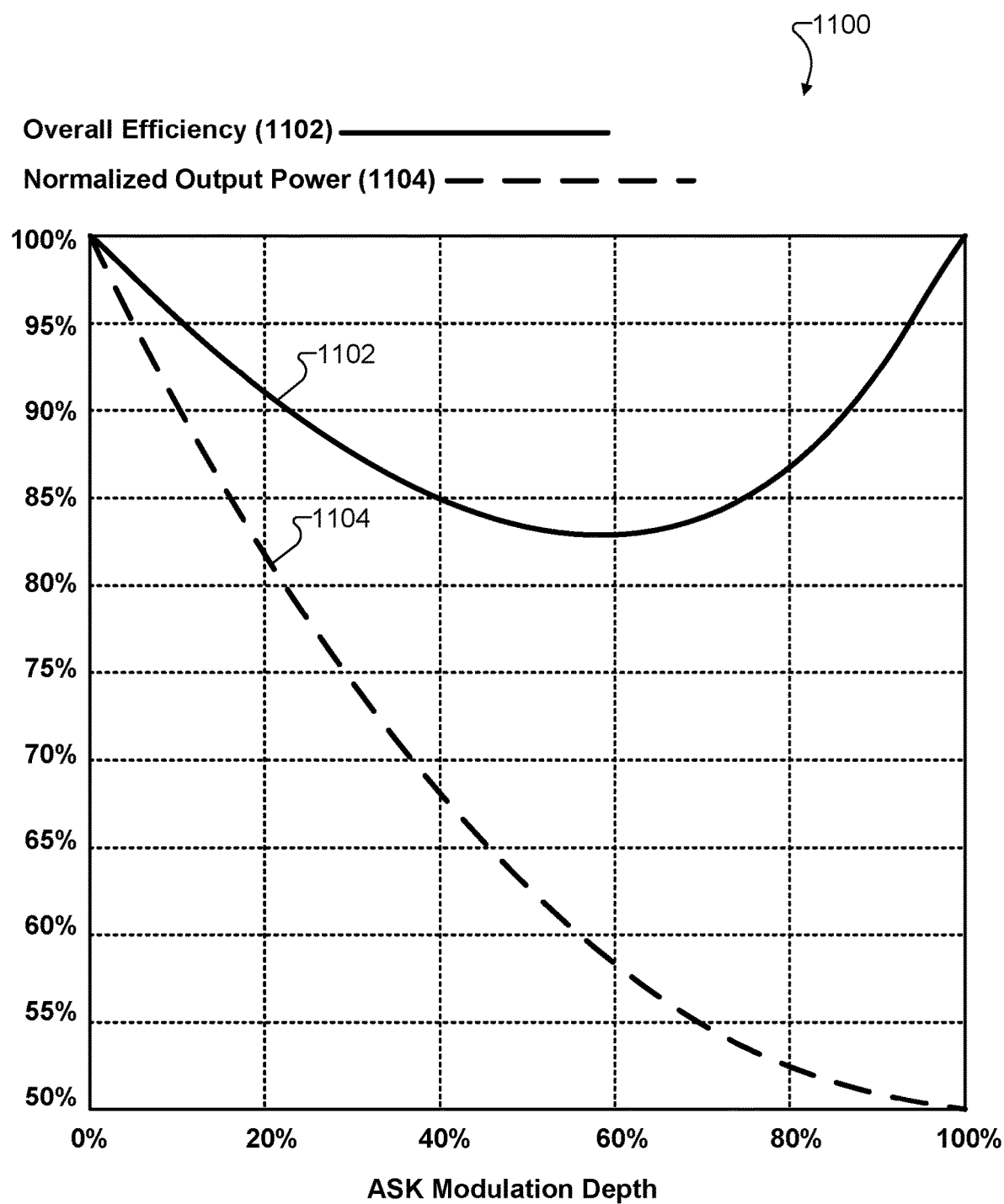
FIG. 11 illustrates a graph showing an overall efficiency and a normalized output power of an exemplary implementation of an ASK modulation system for ASK modulation of a digital data signal onto RF power that is to be wirelessly delivery to a load according to principles described herein.

To illustrate, FIG. 11 shows a graph 1100 illustrating an overall efficiency 1102 and a normalized output power 1104 of an exemplary implementation of ASK modulation system 400 for ASK modulation of digital data signal 112 onto RF power that is to be wirelessly delivered to a load. As shown, various ASK modulation depths from 0% to 100% are shown along the horizontal axis, while overall efficiency and normalized output power are indicated along the vertical axis. The on-off keying modulation performed by modulation system 100 is represented at the far right-hand side of graph 1100 (i.e., where modulation depth is 100%). As shown, this may be very efficient since all of the energy of input DC power 110 may be transmitted without any being wasted by the voltage step-down of a linear regulator circuit. However, only 50% of the possible energy is being transmitted in this case since no RF power is transmitted at all for almost half of the time.

In contrast, by using a relatively low modulation depth such as 10%, the efficiency is almost as good (i.e., approximately 95% of the energy of input DC power 110 is transmitted after approximately 5% is lost in the voltage step-down of hybrid linear regulator circuit 502), but the amount of output power actually transmitted is nearly twice as much as was transmitted by modulation system 100 (i.e., around 90% rather than 50%). Accordingly, ASK modulation system 400 may provide many efficiency and power benefits when used with relatively low modulation depths, as described above. Graph 1100 also illustrates how efficiency and power may be traded off for various other modulation depths that may be supported by a particular implementation.

The systems and methods for ASK modulation of a digital data signal onto RF power that is to be wirelessly delivered to a load may be used in various different contexts and may provide benefits when used in any of various configurations or implementations. As one example, the systems and methods described herein may be used in the context of an implantable medical device such as a cochlear implant system. Referring to ASK modulation system 400 of FIG. 4, for example, power supply 102, ASK modulation controller 402 (e.g., including hybrid linear regulator circuit 502, intermediate DC power switching circuit 504, and/or modulation depth control circuit 508 of FIG. 5), and RF driver circuit 104 may all be included within a sound processor of a cochlear implant system. The sound processor may be external to a patient associated with (e.g., using) the cochlear implant system.

As such, load 106 may be associated with (e.g., may be an implementation of, may be included within, etc.) a cochlear implant of the cochlear implant system. For example, the cochlear implant may be implanted within the patient and may be removably coupled with the sound processor by way of a transcutaneous RF link facilitated by a headpiece of the cochlear implant system. The sound processor may thus provide the RF output power representative of the digital data signal to the load associated with the cochlear implant by way of the transcutaneous RF link.

Moreover, the sound processor of the cochlear implant system may also include at least one electric power cell generating electric power at an electric power cell voltage level, and a switching regulator circuit powered by the electric power at the electric power cell voltage level. For example, the switching regulator circuit may regulate the electric power at the electric power cell voltage level to generate input DC power at a first voltage level (i.e., input DC power 110 used by ASK modulation controller 402 to generate intermediate DC power 404). In some examples, the first voltage level of the input DC power generated by the switching regulator circuit may be a variable voltage level dynamically varying in time within a static voltage range defined by a nonzero minimum voltage level and a maximum voltage level at least two times greater than the minimum voltage level.

Along with the sound processor, the cochlear implant system may also include a microphone that is coupled with the sound processor and configured to detect an audio signal presented to the patient and to generate an electrical signal representative of the audio signal. Accordingly, the switching regulator circuit within the sound processor may receive a power delivery signal representative of a power delivery parameter that is based on an intensity of the audio signal detected by the microphone coupled with the sound processor. In response to receiving the power delivery signal, the switching regulator circuit may generate the input DC power in accordance with the power delivery parameter by causing the variable voltage level of the input DC power to dynamically vary based on the power delivery parameter.

For example, if the microphone detects that the audio signal being presented to the patient (e.g., a voice or other sound in the room the patient is in) is particularly loud, the sound processor may determine that a relatively large amount of power will be used by the cochlear implant to stimulate the patient in accordance with the loud audio signal. Thus, the sound processor may indicate as much to the switching regulator circuit (e.g., by way of the power delivery signal) in a "feed forward" loop (e.g., as opposed to a "feedback" loop in which input may be received from the cochlear implant where the power is being transmitted). The power delivery signal indicating that the relatively large amount of RF power is to be transmitted may cause the switching regulator circuit to generate input DC power at an increased voltage level (i.e., may elevate the first variable voltage level) as long as the intensity (i.e., loudness) of the audio signal presented to the patient persists. However, when the audio signal become more quiet, the sound processor may indicate, by way of the power delivery signal, that the switching regulator circuit may generate input DC power at a lower voltage level (i.e., may decrease the first variable voltage level). As has been described, the voltage range throughout which the first variable voltage level may vary may be relatively wide. For example, the voltage range may be from approximately 0.6 V to approximately 3.0 V in certain examples.

Figure 12:
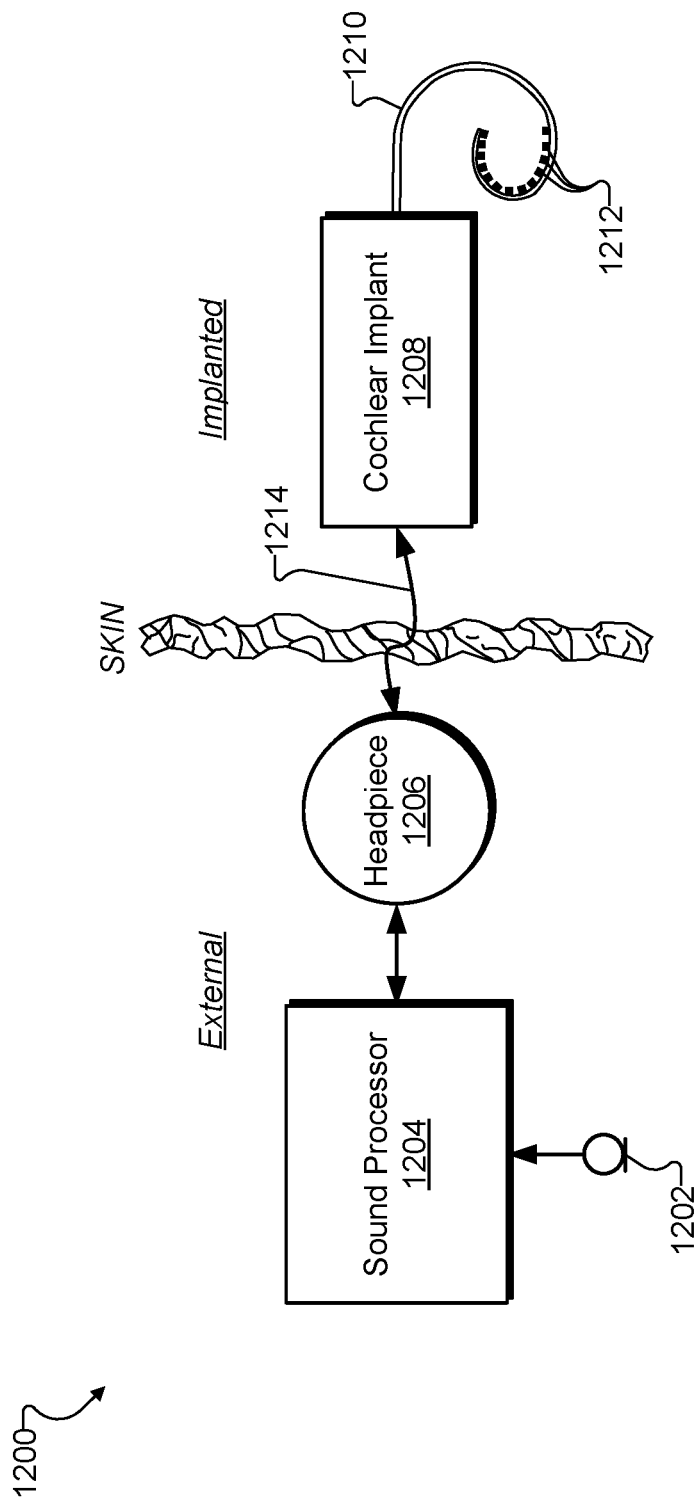
FIG. 12 illustrates an exemplary cochlear implant system according to principles described herein.

To illustrate how the system and methods described herein may apply in a cochlear implant system context, FIG. 12 shows an exemplary cochlear implant system 1200. As shown, cochlear implant system 1200 may include various components configured to be located external to a cochlear implant patient including, but not limited to, a microphone 1202, a sound processor 1204, and a headpiece 1206. Cochlear implant system 1200 may further include various components configured to be implanted within the patient including, but not limited to, a cochlear implant 1208 (also referred to as an implantable cochlear stimulator) and a lead 1210 (also referred to as an intracochlear electrode array) with a plurality of electrodes 1212 disposed thereon. In certain examples, additional or alternative components may be included within cochlear implant system 1200 as may serve a particular implementation. The components shown in FIG. 12 will now be described in more detail.

Microphone 1202 may be configured to detect audio signals presented to the patient and to generate electrical signals representative of the detected audio signals (e.g., for processing by sound processor 1204). Microphone 1202 may be implemented in any suitable manner. For example, microphone 1202 may include a microphone such as a T-MIC™ microphone from Advanced Bionics. Microphone 1202 may be associated with a particular ear of the patient such as by being located in a vicinity of the particular ear (e.g., within the concha of the ear near the entrance to the ear canal). In some examples, microphone 1202 may be held within the concha of the ear near the entrance of the ear canal by a boom or stalk that is attached to an ear hook configured to be selectively attached to sound processor 1204. Additionally or alternatively, microphone 1202 may be implemented by one or more microphones disposed within headpiece 1206, one or more microphones disposed within sound processor 1204, one or more beam-forming microphones, and/or any other suitable microphone or microphones as may serve a particular implementation.

Sound processor 1204 (i.e., one or more components included within sound processor 1204) may be configured to direct cochlear implant 1208 to generate and apply electrical stimulation (also referred to herein as "stimulation current") representative of one or more audio signals (e.g., one or more audio signals detected by microphone 1202, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. While, for the sake of simplicity, electrical stimulation will be described herein as being applied to one or both of the cochleae of a patient, it will be understood that stimulation current may also be applied to other suitable nuclei in the auditory pathway. To this end, sound processor 1204 may process the one or more audio signals in accordance with a selected sound processing strategy or program to generate appropriate stimulation parameters for controlling cochlear implant 1208. Sound processor 1204 may include or be implemented by a behind-the-ear ("BTE") unit, a body worn device, and/or any other sound processing unit as may serve a particular implementation. For example, sound processor 1204 may be implemented by an electro-acoustic stimulation ("EAS") sound processor included in an EAS system configured to provide electrical and acoustic stimulation to a patient.

In some examples, sound processor 1204 may wirelessly transmit stimulation parameters (e.g., in the form of data words included in a forward telemetry sequence) and/or power signals to cochlear implant 1208 by way of a wireless communication link 1214 (e.g., a transcutaneous link) between headpiece 1206 and cochlear implant 1208. It will be understood that communication link 1214 may include a bidirectional communication link and/or one or more dedicated unidirectional communication links. In some examples, sound processor 1204 may execute and operate in accordance with a sound processing program that has been loaded into memory contained within sound processor 1204.

To this end, as described above, sound processor 1204 may include various circuits and elements described herein, such as implementations of power supply 102, ASK modulation controller 402, RF driver 104, and/or components thereof, as well as other circuits and/or elements as may serve a particular implementation. As such, sound processor 1204 may transcutaneously transmit (e.g., by way of headpiece 1206 and wireless communication link 1214) wireless power and wireless data to cochlear implant 1208 in accordance with the systems and methods described herein.

Headpiece 1206 may be communicatively coupled to sound processor 1204 and may include an external antenna (e.g., a coil and/or one or more wireless communication components) configured to facilitate selective wireless coupling of sound processor 1204 to cochlear implant 1208. Headpiece 1206 may additionally or alternatively be used to selectively and wirelessly couple any other external device to cochlear implant 1208. To this end, headpiece 1206 may be configured to be affixed to the patient's head and positioned such that the external antenna housed within headpiece 1206 is communicatively coupled to a corresponding implantable antenna (which may also be implemented by a coil and/or one or more wireless communication components) included within or otherwise associated with cochlear implant 1208. In this manner, wireless data signals and/or wireless power may be wirelessly transmitted between sound processor 1204 and cochlear implant 1208 via communication link 1214.

Cochlear implant 1208 may include any type of implantable stimulator that may be used in association with the systems and methods described herein. For example, cochlear implant 1208 may be implemented by an implantable cochlear stimulator. In some alternative implementations, cochlear implant 1208 may include a brainstem implant and/or any other type of active implant or auditory prosthesis that may be implanted within a patient and configured to apply stimulation to one or more stimulation sites located along an auditory pathway of a patient.

In some examples, cochlear implant 1208 may be configured to generate electrical stimulation representative of an audio signal processed by sound processor 1204 (e.g., an audio signal detected by microphone 1202) in accordance with one or more stimulation parameters transmitted thereto by sound processor 1204. Cochlear implant 1208 may be further configured to apply the electrical stimulation to one or more stimulation sites within the patient via one or more electrodes 1212 disposed along lead 1210 (e.g., by way of one or more stimulation channels formed by electrodes 1212). In some examples, cochlear implant 1208 may include a plurality of independent current sources each associated with a channel defined by one or more of electrodes 1212. In this manner, different stimulation current levels may be applied to multiple stimulation sites simultaneously (also referred to as "concurrently") by way of multiple electrodes 1212.

Cochlear implant 1208 may be powered (e.g., exclusively powered) by RF power transmitted thereto by sound processor 1204 by way of headpiece 1206. As described above, the amount of power cochlear implant 1208 may use to stimulate particular stimulation parameters received by sound processor 1204 may vary (e.g., based on intensity of the audio signal received by microphone 1202). As such, sound processor 1204 may continuously cause the voltage level at which the RF power is transmitted to vary (e.g., by controlling a power delivery signal input to a switching regulator circuit that provides an input DC power) so as to efficiently provide just as much power as cochlear implant 1208 needs.

Figure 13:
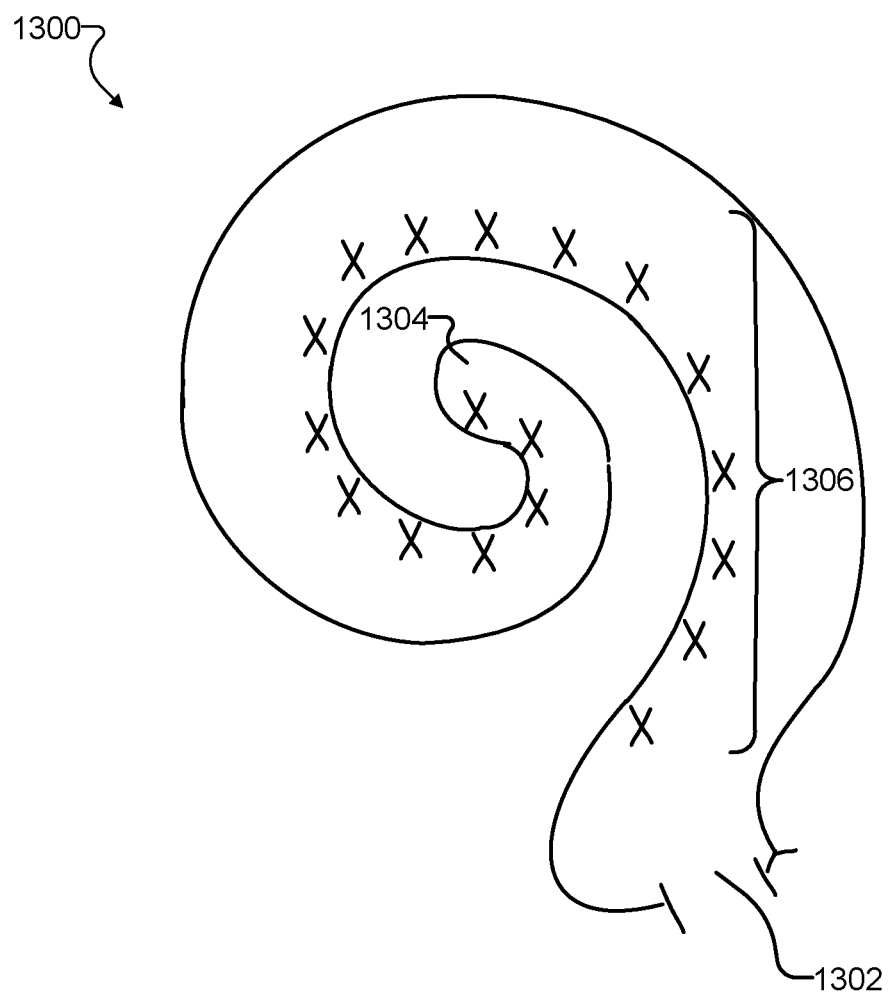
FIG. 13 illustrates a schematic structure of the human cochlea according to principles described herein.

FIG. 13 illustrates a schematic structure of the human cochlea 1300 into which lead 1210 may be inserted. As shown in FIG. 13, cochlea 1300 is in the shape of a spiral beginning at a base 1302 and ending at an apex 1304. Within cochlea 1300 resides auditory nerve tissue 1306, which is denoted by Xs in FIG. 13. Auditory nerve tissue 1306 is organized within cochlea 1300 in a tonotopic manner. That is, relatively low frequencies are encoded at or near apex 1304 of cochlea 1300 (referred to as an "apical region") while relatively high frequencies are encoded at or near base 1302 (referred to as a "basal region"). Hence, each location along the length of cochlea 1300 corresponds to a different perceived frequency. Cochlear implant system 1200 may therefore be configured to apply electrical stimulation to different locations within cochlea 1300 (e.g., different locations along auditory nerve tissue 1306) to provide a sensation of hearing to the patient. For example, when lead 1210 is properly inserted into cochlea 1300, each of electrodes 1212 may be located at a different cochlear depth within cochlea 1300 (e.g., at a different part of auditory nerve tissue 1306) such that stimulation current applied to one electrode 1212 may cause the patient to perceive a different frequency than the same stimulation current applied to a different electrode 1212 (e.g., an electrode 1212 located at a different part of auditory nerve tissue 1306 within cochlea 1300).

Figure 14:
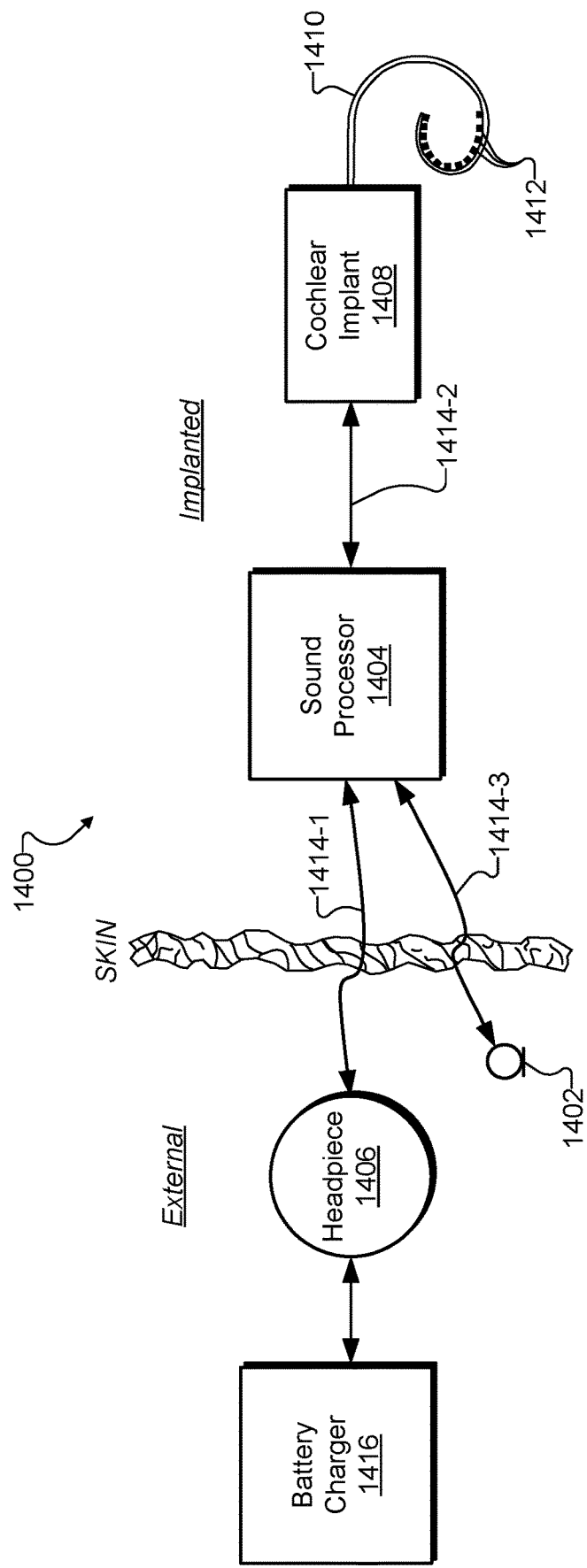
FIG. 14 illustrates another exemplary cochlear implant system according to principles described herein.

A specific example of one context in which the systems and methods described herein may be used was described above in relation to cochlear implant system 1200. As another example, FIG. 14 shows another exemplary cochlear implant system 1400. Cochlear implant system 1400 includes many of the same types of components described above in relation to cochlear implant system 1200, each of which may perform similar or identical functionality as described. For example, cochlear implant system 1400 includes a microphone 1402 similar to microphone 1202, a sound processor 1404 similar to sound processor 1204, a headpiece 1406 similar to headpiece 1206, a cochlear implant 1408 similar to cochlear implant 1208, a lead 1410 with electrodes 1412 similar to lead 1210 with electrodes 1212, and communication links 1414 (i.e., communication links 1414-1, 1414-2, and 1414-3) similar to communication link 1214.

However, in contrast to cochlear implant system 1200, cochlear implant system 1400 may be a fully implanted (or nearly fully implanted) cochlear implant system in the sense that, unlike cochlear implant system 1200, all or nearly all of the components of cochlear implant system 1400 may be implanted within the patient. Specifically, sound processor 1404 is implanted within the patient along with cochlear implant 1408, lead 1410, and electrodes 1412. As such, communication link 1414-2 between sound processor 1404 and cochlear implant 1408 is also implanted within the patient. In some examples, rather than being a wireless communication link, communication link 1414-2 may be a wired communication link or may be omitted (e.g., in an example where sound processor 1404 and cochlear implant 1408 are integrated into a single device implanted within the patient).

As shown, microphone 1402 and headpiece 1406 may still be external to the patient. For example, microphone 1402 may be better able to detect audio signals presented to the patient if the audio signals do not have to propagate through the patient's skin before being detected. Headpiece 1406 may be used to facilitate a battery charger 1416 to transmit RF power to sound processor 1404 (e.g., by way of communication link 1414-1) to recharge a battery included within sound processor 1404. It will be understood that battery charger 1416 and/or headpiece 1406 may not be included within the cochlear implant system per se, but rather may be removably connected to the cochlear implant system when the battery is to be recharged.

The systems and methods for ASK modulation of a digital data signal onto RF power that is to be wirelessly delivered to a load may be employed with respect to any of communication links 1414 shown in FIG. 14. For example, the load to which RF power is to be delivered may be associated with cochlear implant 1408 and the RF power may be delivered from sound processor 1404 by way of communication link 1414-2. Specifically, cochlear implant 1408 may be separate from sound processor 1404 even though cochlear implant 1408 is implanted within the patient along with sound processor 1404 (e.g., for the purpose of keeping sound processor 1404 and the battery included therein near the surface of the skin for easier battery replacement). Cochlear implant 1408 may be coupled with sound processor 1404 by way of communication link 1414-2 such that digital data modulated onto RF power may be wirelessly delivered from sound processor 1404 to cochlear implant 1408. In other examples, because communication link 1414-2 does not traverse the skin, communication link 1414-2 may instead by implemented as a wired baseband link.

As another example, the load to which RF power is to be delivered may be associated with sound processor 1404 and the RF power may be delivered from battery charger 1416 (e.g., which may be configured to charge a battery included within sound processor 1404). Specifically, sound processor 1404 may be coupled with battery charger 1416 by way of headpiece 1406 and by way of communication link 1414-1 such that digital data modulated onto RF power may be wirelessly delivered from battery charger 1416 to sound processor 1404. For example, sound processor 1404 may require that only a particular type of battery charger be used for recharging the battery included within sound processor 1404. As such, battery charger 1416 may wirelessly deliver handshaking data (e.g., data representative of an identity of battery charger 1416, charging characteristics of battery charger 1416, a passcode required for charging, or the like).

As yet another example, the load to which RF power is to be delivered may be associated with microphone 1402 and the RF power may be delivered from sound processor 1404. Specifically, microphone 1402 may be coupled with sound processor 1404 by way of communication link 1414-3 such that digital data modulated onto RF power may be wirelessly delivered from sound processor 1404 to microphone 1402. For example, along with powering microphone 1402, sound processor 1404 may transmit data to microphone 1402 representative of interrogations as to an identity of microphone 1402, technical characteristics of microphone 1402, and the like.

While two specific examples of cochlear implant systems have been illustrated and described, it will be understood that the systems and methods for ASK modulation of a digital data signal onto RF power that is to be wirelessly delivered to a load described herein may also be used in other contexts. For example, the systems and methods described herein could be used to transmit wireless power and wireless data to other types of implantable medical devices other than cochlear implants. Similarly, the systems and methods described herein could be used to transmit wireless power and wireless data to, for example, strain gages in a motor shaft (e.g., to monitor stress applied to the motor shaft during testing), or to facilitate similar test and automation applications relating to other technologies (e.g., oil drilling, windmills, etc.).

Figure 15:
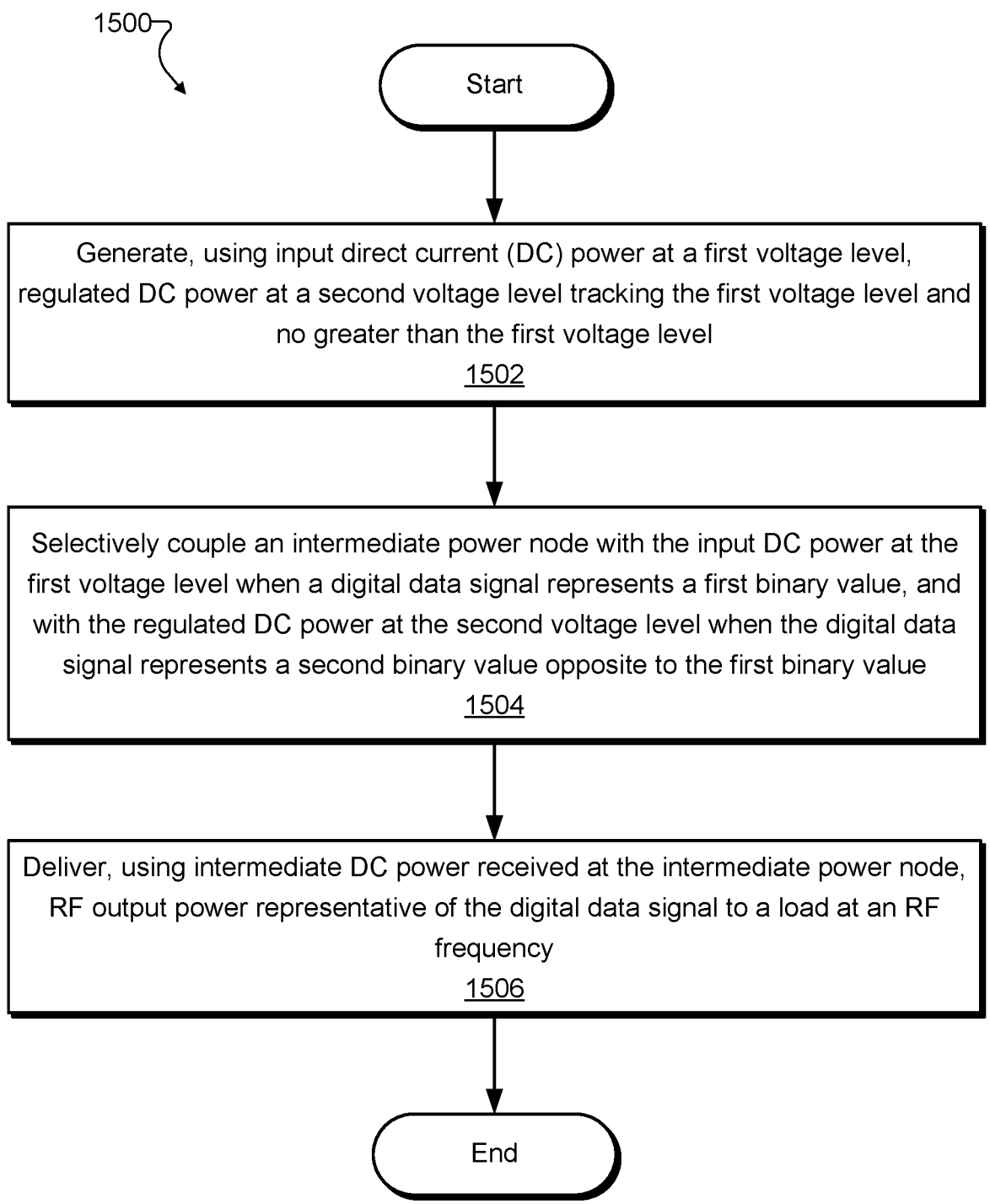
FIGS. 15-16 illustrate exemplary methods for ASK modulation of a digital data signal onto RF power that is to be wirelessly delivered to a load according to principles described herein.

FIG. 15 illustrates an exemplary method for ASK modulation of a digital data signal onto RF power that is to be wirelessly delivered to a load. One or more of the operations shown in FIG. 15 may be performed by ASK modulation system 400 and/or any implementation thereof. While FIG. 15 illustrates exemplary operations according to one embodiment, other embodiments may omit, add to, reorder, and/or modify any of the operations shown in FIG. 15.

In operation 1502, an ASK modulation system (e.g., a linear regulator circuit included within the ASK modulation system) may generate regulated DC power. For example, the linear regulator circuit may be powered by input DC power at a first voltage level and may use the input DC power to generate the regulated DC power at a second voltage level that is tracking the first voltage level and no greater than the first voltage level. Operation 1502 may be performed in any of the ways described herein.

In operation 1504, the ASK modulation system (e.g., an intermediate DC power switching circuit within the ASK modulation system) may selectively couple an intermediate power node with DC power based on a digital data signal received by the intermediate DC power switching circuit. For example, the ASK modulation system may selectively couple the intermediate power node with the input DC power at the first voltage level when the digital data signal represents a first binary value, and with the regulated DC power at the second voltage level when the digital data signal represents a second binary value opposite to the first binary value. Operation 1504 may be performed in any of the ways described herein.

In operation 1506, the ASK modulation system (e.g., an RF driver circuit that is included within the ASK modulation system) may deliver RF output power representative of the digital data signal to a load at an RF frequency. For example, the RF driver circuit may be powered by intermediate DC power received by the RF driver circuit at the intermediate power node. Operation 1506 may be performed in any of the ways described herein.

Figure 16:
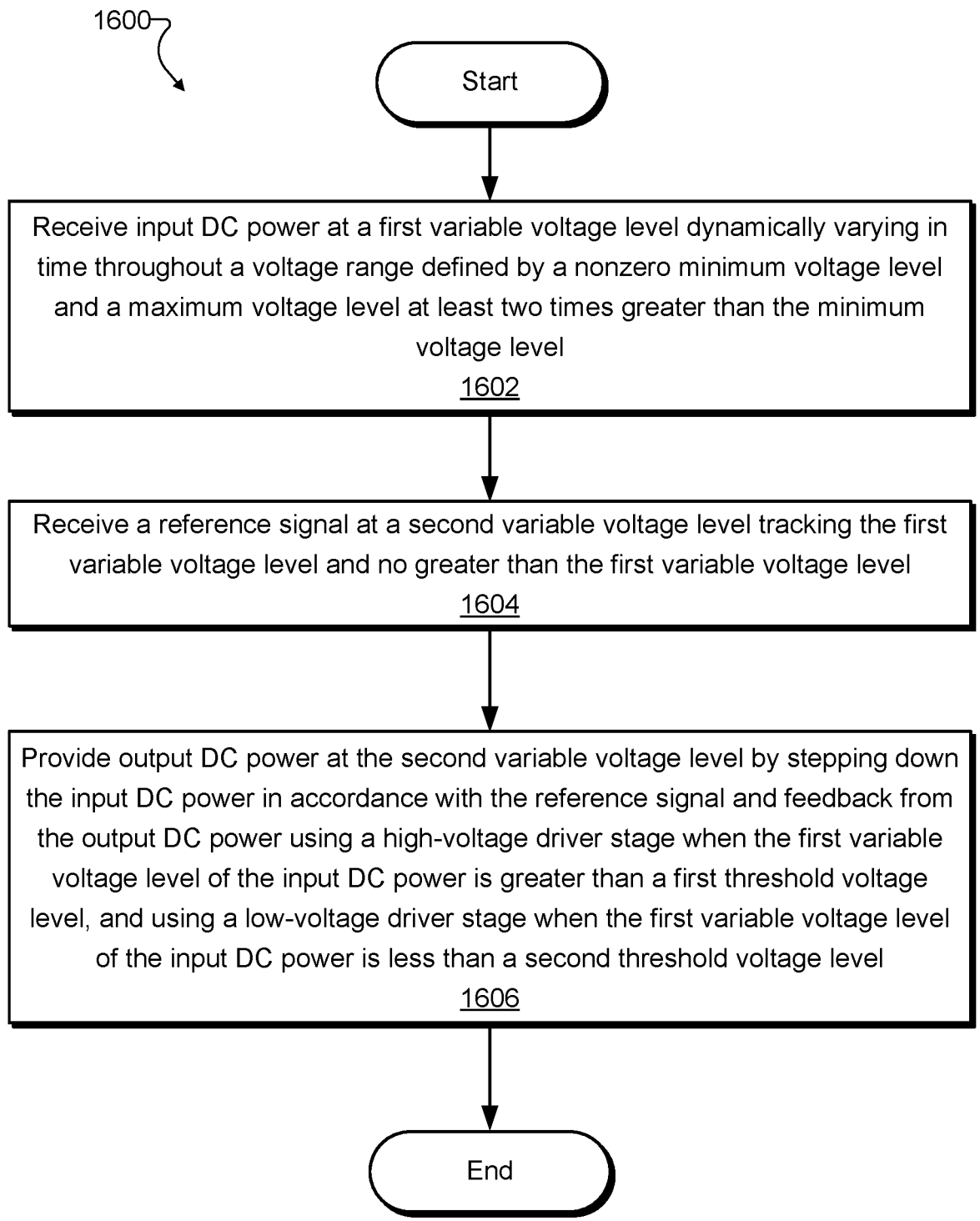

FIG. 16 illustrates another exemplary method for ASK modulation of a digital data signal onto RF power that is to be wirelessly delivered to a load. One or more of the operations shown in FIG. 16 may be performed by ASK modulation system 400 and/or any implementation thereof. While FIG. 16 illustrates exemplary operations according to one embodiment, other embodiments may omit, add to, reorder, and/or modify any of the operations shown in FIG. 16.

In operation 1602, a linear regulator circuit included within an ASK modulation system may receive (e.g., at an input DC power node of the linear regulator circuit) input DC power at a first variable voltage level. The first variable voltage level may dynamically vary in time throughout a voltage range. For example, the voltage range may be defined by a nonzero minimum voltage level and a maximum voltage level that is at least two times greater than the minimum voltage level. Operation 1602 may be performed in any of the ways described herein.

In operation 1604, the linear regulator circuit may receive (e.g., at a reference signal node of the linear regulator circuit) a reference signal at a second variable voltage level. For example, the second variable voltage level may track the first variable voltage level and may be no greater than the first variable voltage level. Operation 1604 may be performed in any of the ways described herein.

In operation 1606, the linear regulator circuit may provide (e.g., at an output DC power node of the linear regulator circuit) output DC power at the second variable voltage level. Operation 1606 may be performed in any of the ways described herein. For example, the providing of the output DC power in operation 1606 may include driving the output DC power at the output DC power node by stepping down the input DC power in accordance with the reference signal and feedback from the output DC power (e.g., a feedback voltage of the output DC power or the like). In particular, the driving of the output DC power may be performed by a high-voltage driver stage included within the linear regulator circuit when the first variable voltage level of the input DC power is greater than a first threshold voltage level, and by a low-voltage driver stage included within the linear regulator circuit and when the first variable voltage level of the input DC power is less than a second threshold voltage level.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a linear regulator circuit including
      an input direct current (DC) power node to which input DC power at a first voltage level is coupled, the first voltage level dynamically varying in time throughout a voltage range defined by a nonzero minimum voltage level and a maximum voltage level at least two times greater than the minimum voltage level,
      an output DC power node by way of which the linear regulator circuit provides regulated DC power at a second voltage level tracking the first voltage level and no greater than the first voltage level, a high-voltage driver stage coupled to the input DC power node and the output DC power node, the high-voltage driver stage configured to drive, when the first voltage level of the input DC power is greater than a first threshold voltage level, the regulated DC power at the output DC power node by stepping down the input DC power from the first voltage level to the second voltage level, and a low-voltage driver stage coupled to the input DC power node and the output DC power node, the low-voltage driver stage configured to drive, when the first voltage level of the input DC power is less than a second threshold voltage level different from the first threshold voltage level, the regulated DC power at the output DC power node by stepping down the input DC power from the first voltage level to the second voltage level;

an intermediate DC power switching circuit that receives a digital data signal and selectively couples, based on the digital data signal, an intermediate power node with the input DC power at the first voltage level when the digital data signal represents a first binary value, and the regulated DC power at the second voltage level when the digital data signal represents a second binary value opposite to the first binary value; and a radio frequency (RF) driver circuit powered by intermediate DC power received by the RF driver circuit at the intermediate power node, the RF driver circuit delivering RF output power representative of the digital data signal to a load at an RF carrier frequency.

2. The system of claim 1, wherein:
the linear regulator circuit further includes a reference signal node to which a reference signal at the second voltage level is coupled;
the high-voltage driver stage is further coupled to the reference signal node;
the high-voltage driver stage is configured to perform the stepping down of the input DC power in accordance with the reference signal and feedback from the regulated DC power;
the low-voltage driver stage is further coupled to the input DC power node, the reference signal node; and
the low-voltage driver stage is configured to perform the stepping down of the input DC power in accordance with the reference signal and the feedback from the regulated DC power.

3. The system of claim 2, wherein the linear regulator circuit further includes:
a p-type transistor included within the high-voltage driver stage; and
an n-type transistor included within the low-voltage driver stage;
wherein
when the first voltage level of the input DC power is greater than the first threshold voltage level, the p-type transistor applies, to the input DC power in accordance with a first control signal based on the reference signal and based on the feedback from the regulated DC power, a first step-down resistance to step down the input DC power at the first voltage level to drive the regulated DC power at the second voltage level, and
when the first voltage level of the input DC power is less than the second threshold voltage level, the n-type transistor applies, to the input DC power in accordance with a second control signal based on the reference signal and based on the feedback from the regulated DC power, a second step-down resistance to step down the input DC power at the first voltage level to drive the regulated DC power at the second voltage level.

4. The system of claim 3, wherein the linear regulator circuit further includes:
a first differential amplifier included within the high-voltage driver stage; and
a second differential amplifier included within the low-voltage driver stage;
wherein
the first differential amplifier derives the first control signal from the reference signal and from the feedback from the regulate DC power by amplifying a positive voltage difference between the regulated DC power and the reference signal, and
the second differential amplifier derives the second control signal from the reference signal and from the feedback from the regulated DC power by amplifying a negative voltage difference between the regulated DC power and the reference signal.

5. The system of claim 3, wherein:
the p-type transistor included within the high-voltage driver stage is a p-channel field effect transistor (FET) having a gate terminal coupled with the first control signal, a source terminal coupled with the input DC power, and a drain terminal coupled with the regulated DC power; and
the n-type transistor included within the low-voltage driver stage is an n-channel FET having a gate terminal coupled with the second control signal, a source terminal coupled with the regulated DC power, and a drain terminal coupled with the input DC power.

6. The system of claim 1, wherein the high-voltage driver stage and the low-voltage driver stage are configured to mutually drive the regulated DC power at the output DC power node when the first voltage level of the input DC power is less than the first threshold voltage level and greater than the second threshold voltage level.

7. The system of claim 1, wherein the intermediate DC power switching circuit includes:
a high-voltage switching stage coupled between the input and output DC power nodes and the intermediate power node, the high-voltage switching stage configured to drive, when the first voltage level of the input DC power is greater than a third threshold voltage level, toggled output DC power at the intermediate power node by switching, in accordance with the digital data signal, between coupling the intermediate power node with the input DC power and coupling the intermediate power node with the regulated DC power; and
a low-voltage switching stage coupled between the input and output DC power nodes and the intermediate power node in parallel with the high-voltage switching stage, the low-voltage switching stage configured to drive, when the first voltage level of the input DC power is less than the third threshold voltage level, the toggled output DC power at the intermediate power node by switching, in accordance with the digital data signal, between coupling the intermediate power node with the input DC power and coupling the intermediate power node with the regulated DC power.

8. The system of claim 7, wherein the low-voltage switching stage includes:
a first thin-oxide FET configured to operate at voltage levels less than the third threshold voltage level;

a first thick-oxide FET coupled between the first thin-oxide FET and the input DC power node, the first thick-oxide FET configured to isolate the first thin-oxide FET from the input DC power when the first voltage level is greater than the third threshold voltage level;

a second thin-oxide FET configured to operate at voltage levels less than the third threshold voltage level;

a second thick-oxide FET coupled between the second thin-oxide FET and the output DC power node, the second thick-oxide FET configured to isolate the second thin-oxide FET from the regulated DC power when the first voltage level is greater than the third threshold voltage level; and a third thick-oxide FET coupled between the first and second thin-oxide FETs and the intermediate power node, the third thick-oxide FET configured to isolate the first and second thin-oxide FETs from the toggled output DC power when the first voltage level is greater than the third threshold voltage level.

9. The system of claim 1, further comprising:

at least one electric power cell generating electric power at an electric power cell voltage level; and a switching regulator circuit powered by the electric power at the electric power cell voltage level, the switching regulator circuit regulating the electric power at the electric power cell voltage level to generate the input DC power at the first voltage level;

wherein the first voltage level of the input DC power generated by the switching regulator circuit is a variable voltage level dynamically varying in time within a static voltage range defined by a nonzero minimum voltage level and a maximum voltage level at least two times greater than the minimum voltage level.

10. The system of claim 1, further comprising a modulation depth control circuit that generates a reference signal at the second voltage level based on the first voltage level of the input DC power and based on a modulation depth select signal representative of a particular amplitude shift keying (ASK) modulation depth in a plurality of ASK modulation depths supported by the modulation depth control circuit.

11. The system of claim 10, wherein the modulation depth control circuit includes:

circuitry implementing a resistor ladder that divides the first voltage level of the input DC power into a plurality of potential reference signals each tracking the first voltage level and no greater than the first voltage level; and circuitry implementing a multiplexer with a plurality of signal inputs, at least one selection input, and a signal output;

wherein
  each of the potential reference signals in the plurality of potential reference signals is coupled with a respective signal input in the plurality of signal inputs,
  the modulation depth select signal is a digital signal that is coupled with the at least one selection input, and
  the signal output is the generated reference signal at the second voltage level.

12. The system of claim 10, wherein:

the modulation depth control circuit includes circuitry implementing a variable resistor, the variable resistor having a signal input, a selection input, and a signal output;

the input DC power at the first voltage level is coupled with the signal input;

the modulation depth select signal is an analog signal that is coupled to the selection input; and the signal output is the generated reference signal at the second voltage level.

13. The system of claim 10, wherein the modulation depth select signal is automatically altered to switch from the particular ASK modulation depth to a different ASK modulation depth so as to change an amount of RF output power that is to be delivered to the load.

14. The system of claim 1, wherein:

the RF driver circuit, the linear regulator circuit, and the intermediate DC power switching circuit are all included within a sound processor of a cochlear implant system, the sound processor external to a patient associated with the cochlear implant system;

the load is associated with a cochlear implant of the cochlear implant system, the cochlear implant implanted within the patient and removably coupled with the sound processor by way of a transcutaneous RF link facilitated by a headpiece of the cochlear implant system; and the sound processor provides the RF output power representative of the digital data signal to the load associated with the cochlear implant by way of the transcutaneous RF link.

15. A cochlear implant system comprising:

a microphone configured to detect an audio signal presented to a patient associated with the cochlear implant system and to generate an electrical signal representative of the audio signal;

a cochlear implant implanted within the patient; and a sound processor communicatively coupled with the microphone and the cochlear implant, the sound processor including
  at least one electric power cell generating electric power at an electric power cell voltage level,
  a switching regulator circuit powered by the electric power at the electric power cell voltage level, the switching regulator circuit
    receiving a power delivery signal representative of a power delivery parameter, the power delivery parameter based on an intensity of the audio signal detected by the microphone coupled with the sound processor, and
    regulating the electric power at the electric power cell voltage level to generate input direct current (DC) power at a first variable voltage level in accordance with the power delivery parameter, the first variable voltage level dynamically varying, in time and based on the power delivery parameter, within a static voltage range defined by a nonzero minimum voltage level and a maximum voltage level at least two times greater than the minimum voltage level,
  a linear regulator circuit including
    an input DC power node to which the input DC power at the first variable voltage level is coupled,
    an output DC power node by way of which the linear regulator circuit provides regulated DC power at a second variable voltage level tracking the first variable voltage level and no greater than the first variable voltage level,
    a high-voltage driver stage coupled to the input DC power node and the output DC power node, the high-voltage driver stage configured to drive, when the first variable voltage level of the input DC power is greater than a first threshold voltage level, the regulated DC power at the output DC power node by stepping down the input DC power from the first variable voltage level to the second variable voltage level, and a low-voltage driver stage coupled to the input DC power node and the output DC power node, the low-voltage driver stage configured to drive, when the first variable voltage level of the input DC power is less than a second threshold voltage level different from the first threshold voltage level, the regulated DC power at the output DC power node by stepping down the input DC power from the first variable voltage level to the second variable voltage level, a modulation depth control circuit that generates a reference signal at the second variable voltage level based on the first variable voltage level of the input DC power and based on a modulation depth select signal representative of a particular amplitude shift keying (ASK) modulation depth in a plurality of ASK modulation depths supported by the modulation depth control circuit, an intermediate DC power switching circuit that receives a digital data signal based on the electrical signal and that selectively couples, based on the digital data signal, an intermediate power node with
the input DC power at the first variable voltage level when the digital data signal represents a first binary value, and
the regulated DC power at the second variable voltage level when the digital data signal represents a second binary value opposite to the first binary value, and a radio frequency (RF) driver circuit powered by intermediate DC power received by the RF driver circuit at the intermediate power node, the RF driver circuit delivering RF output power representative of the digital data signal to the cochlear implant at an RF carrier frequency.

16. The cochlear implant system of claim 15, wherein:
the linear regulator circuit further includes a reference signal node to which the reference signal at the second variable voltage level is coupled;
the high-voltage driver stage is further coupled to the reference signal node;
the high-voltage driver stage is configured to perform the stepping down of the input DC power in accordance with the reference signal and feedback from the regulated DC power;
the low-voltage driver stage is further coupled to the reference signal node; and
the low-voltage driver stage is configured to perform the stepping down of the input DC power in accordance with the reference signal and the feedback from the regulated DC power.

17. The cochlear implant system of claim 16, wherein the linear regulator circuit included within the sound processor further includes:
a p-type transistor included within the high-voltage driver stage; and
an n-type transistor included within the low-voltage driver stage;
wherein
when the first variable voltage level of the input DC power is greater than the first threshold voltage level, the p-type transistor applies, to the input DC power in accordance with a first control signal based on the reference signal and based on the feedback from the regulated DC power, a first step-down resistance to step down the input DC power at the first variable voltage level to drive the regulated DC power at the second variable voltage level, and
when the first variable voltage level of the input DC power is less than the second threshold voltage level, the n-type transistor applies, to the input DC power in accordance with a second control signal based on the reference signal and based on the feedback from the regulated DC power, a second step-down resistance to step down the input DC power at the first variable voltage level to drive the regulated DC power at the second variable voltage level.

18. A method comprising:
generating, by a linear regulator circuit that is included within an amplitude shift keying (ASK) modulation system and is powered by input direct current (DC) power at a first voltage level, regulated DC power at a second voltage level tracking the first voltage level and no greater than the first voltage level;
selectively coupling, by an intermediate DC power switching circuit that is included within the ASK modulation system and based on a digital data signal received by the intermediate DC power switching circuit, an intermediate power node with
the input DC power at the first voltage level when the digital data signal represents a first binary value, and
the regulated DC power at the second voltage level when the digital data signal represents a second binary value opposite to the first binary value; and
delivering, by a radio frequency (RF) driver circuit that is included within the ASK modulation system and is powered by intermediate DC power received by the RF driver circuit at the intermediate power node, RF output power representative of the digital data signal to a load at an RF frequency;
wherein the linear regulator circuit includes:
an input DC power node to which the input DC power at the first voltage level is coupled, the first voltage level dynamically varying in time throughout a voltage range defined by a nonzero minimum voltage level and a maximum voltage level at least two times greater than the minimum voltage level,
an output DC power node by way of which the linear regulator circuit provides the regulated DC power at a second voltage level tracking the first voltage level and no greater than the first voltage level,
a high-voltage driver stage coupled to the input DC power node and the output DC power node, the high-voltage driver stage configured to drive, when the first voltage level of the input DC power is greater than a first threshold voltage level, the regulated DC power at the output DC power node by stepping down the input DC power from the first voltage level to the second voltage level, and
a low-voltage driver stage coupled to the input DC power node and the output DC power node, the low-voltage driver stage configured to drive, when the first voltage level of the input DC power is less than a second threshold voltage level different from the first threshold voltage level, the regulated DC power at the output DC power node by stepping down the input DC power from the first voltage level to the second voltage level.

19. The method of claim 18, wherein:
the linear regulator circuit further includes a reference signal node to which a reference signal at the second voltage level is coupled;
the high-voltage driver stage is further coupled to the reference signal node;
the high-voltage driver stage is configured to perform the stepping down of the input DC power in accordance with the reference signal and feedback from the regulated DC power;
the low-voltage driver stage is further coupled to the reference signal node; and
the low-voltage driver stage is configured to perform the stepping down of the input DC power in accordance with the reference signal and the feedback from the regulated DC power.

20. The method of claim 19, wherein the linear regulator circuit performing the generating of the regulated DC power further includes:
a p-type transistor included within the high-voltage driver stage; and
an n-type transistor included within the low-voltage driver stage;
wherein
when the first voltage level of the input DC power is greater than the first threshold voltage level, the p-type transistor applies, to the input DC power in accordance with a first control signal based on the reference signal and based on the feedback from the regulated DC power, a first step-down resistance to step down the input DC power at the first voltage level to drive the regulated DC power at the second voltage level, and
when the first voltage level of the input DC power is less than the second threshold voltage level, the n-type transistor applies, to the input DC power in accordance with a second control signal based on the reference signal and based on the feedback from the regulated DC power, a second step-down resistance to step down the input DC power at the first voltage level to drive the regulated DC power at the second voltage level.

* * * * *